(12) United States Patent
Novak

(10) Patent No.: US 11,311,735 B2
(45) Date of Patent: Apr. 26, 2022

(54) IMPLANTABLE POUCH WITH SEGMENTAL LAMINATION STRUCTURE, AND RELATED METHODS OF MANUFACTURE AND USE

(71) Applicant: Cook Biotech Incorporated, West Lafayette, IN (US)

(72) Inventor: Tyler Novak, Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 0 days.

(21) Appl. No.: 16/251,335

(22) Filed: Jan. 18, 2019

(65) Prior Publication Data
US 2019/0351241 A1 Nov. 21, 2019

(51) Int. Cl.
*A61N 1/375* (2006.01)
*A61N 1/39* (2006.01)
*A61F 2/00* (2006.01)

(52) U.S. Cl.
CPC ....... *A61N 1/3758* (2013.01); *A61N 1/37512* (2017.08); *A61N 1/39* (2013.01); *A61F 2/0063* (2013.01)

(58) Field of Classification Search
None
See application file for complete search history.

(56) References Cited

FOREIGN PATENT DOCUMENTS

WO WO-2012018680 A1 * 2/2012 ......... A61L 27/3808

* cited by examiner

*Primary Examiner* — Jessica Worsham
(74) *Attorney, Agent, or Firm* — Woodard Emhardt Henry Reeves & Wagner LLP

(57) ABSTRACT

Described are implantable pouch products having a segmental lamination structure that provides an interior pocket for receiving a medical device, for example an electronic medical device such as a cardiac pacemaker or defibrillator. Also described are methods for making and using such products.

13 Claims, 11 Drawing Sheets

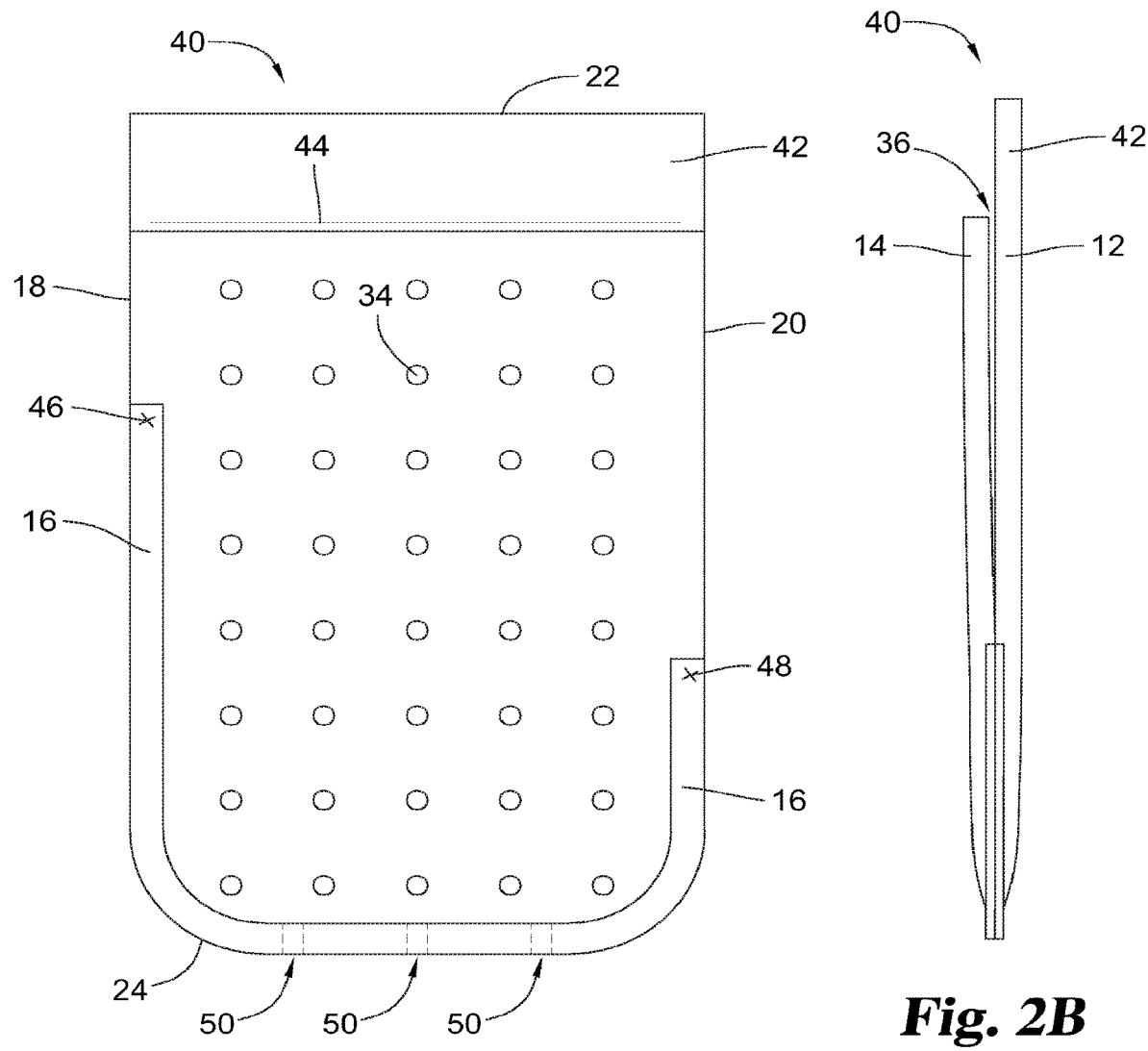
*Fig. 2A*
*Fig. 2B*
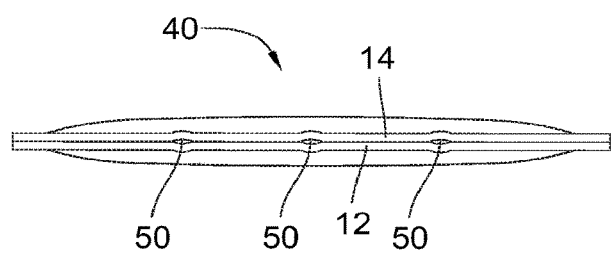
*Fig. 2C*

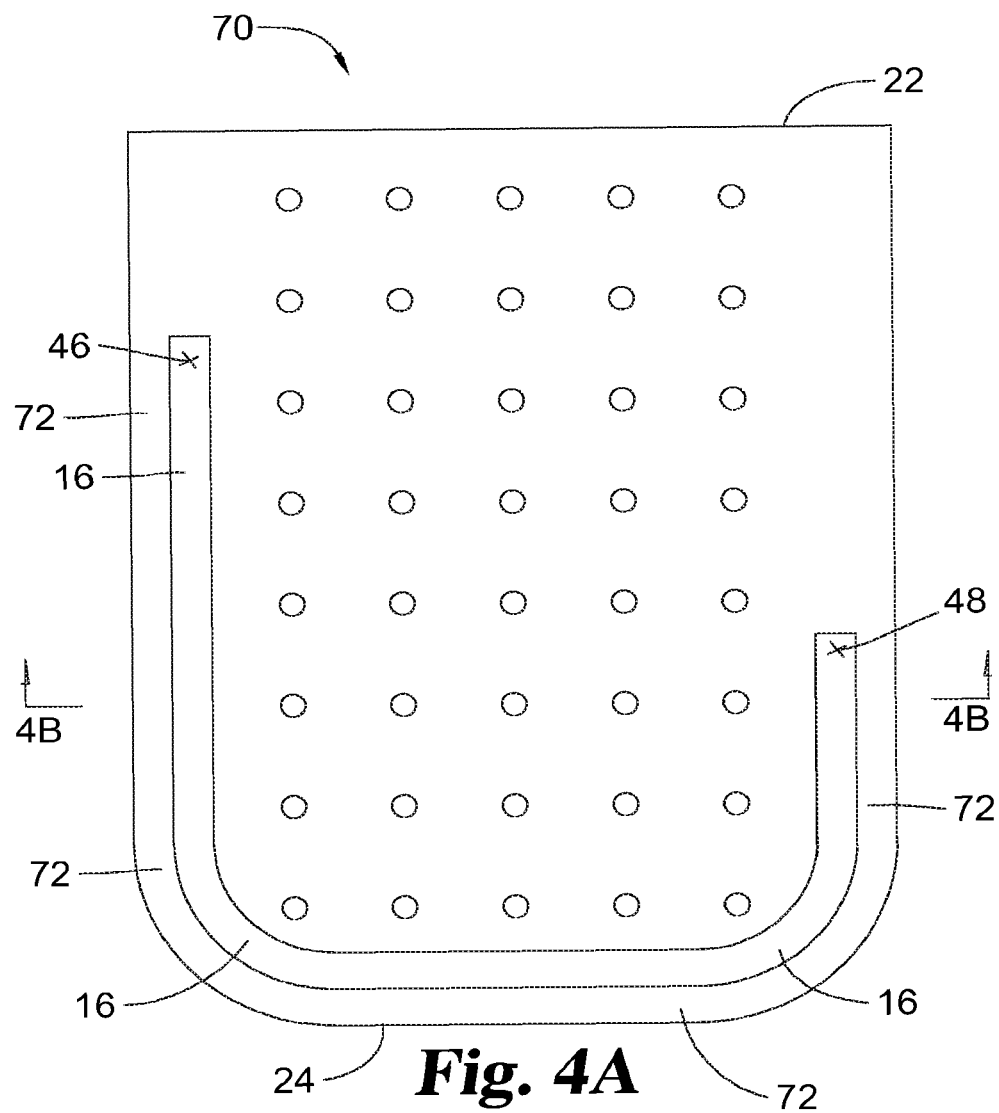
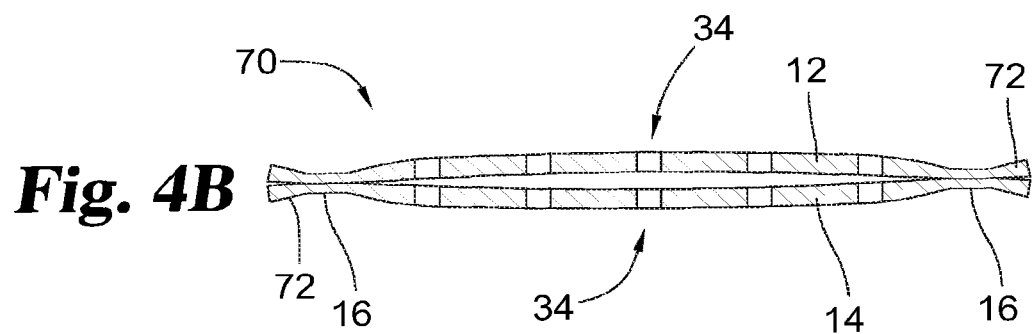
Fig. 4A
Fig. 4B

IMPLANTABLE POUCH WITH SEGMENTAL LAMINATION STRUCTURE, AND RELATED METHODS OF MANUFACTURE AND USE

REFERENCE TO RELATED APPLICATION

The present application claims the benefit of priority of U.S. Provisional Patent Application Ser. No. 62/363,797 filed Jul. 18, 2016, which is hereby incorporated herein by reference in its entirety.

BACKGROUND

In certain aspects, the present disclosure relates to implantable medical devices that define inner pockets. In some more particular aspects, the present disclosure relates to implantable medical devices in the form of pouches designed to receive other medical devices, such as implantable pacing or defibrillation devices.

As further background, the medical industry has developed a variety of implantable devices and systems for sensing and/or affecting bodily function upon implantation and/or for carrying out various other functions in the body. These include but are not limited to pacing devices, defibrillators, implantable access systems, monitors, stimulators including neurostimulators, ventricular assist devices, pain pumps, infusion pumps and other implantable objects or systems or components thereof, for example, those used to deliver energy and/or substances to the body and/or to help monitor bodily function.

Typically, cardiac pacing by an artificial pacemaker delivers a stimulus to the heart when its own natural pacemaker and/or conduction system fails to provide synchronized atrial and ventricular contractions at desirable rates and intervals. Such pacing provides relief from symptoms and even life support for hundreds of thousands of patients.

Cardiac pacing is usually performed by a pulse generator implanted subcutaneously or sub-muscularly in or near a patient's pectoral or abdominal region. The generator usually connects to the proximal end of one or more implanted leads, the distal end of which contains one or more electrodes to be positioned at one or more cardiac locations.

There remain needs for improved or alternative products to promote and/or facilitate the successful implantation of medical devices and systems in the body, as well as methods for preparing and utilizing such products. The present invention, in certain embodiments, is addressed to those needs.

SUMMARY

In one embodiment, provided is an implantable pouch product. The product includes a first collagen-containing wall material defining a first side of the pouch product and a second collagen-containing wall material defining a second side of the pouch product. A first segment of the first collagen-containing wall material is laminated to a first segment of the second collagen-containing wall material to define a pocket periphery laminate material (sometimes referred to herein as a "flange" material). A pocket is defined between a second segment of the first collagen-containing wall material and a second segment of the second collagen-containing wall material that are not laminated to one another, the pocket being bounded by the pocket periphery laminate material. The first segment of the first collagen-containing wall material comprises lyophilized collagen-containing wall material having a first average density, and the first segment of the second wall material comprises lyophilized collagen-containing wall material having a second average density. The pocket periphery laminate material has a third average density, with such third average density being greater than the first average density and the second average density.

In another embodiment, provided is an implantable pouch product including a first wall material defining a first side of the pouch product and a second wall material defining a second side of the pouch product. A first segment of the first wall material is laminated to a first segment of the second wall material to define a pocket periphery laminate material (sometimes referred to herein as a "flange" material). A pocket is defined between a second segment of the first wall material and a second segment of the second wall material that are not laminated to one another, the pocket being bounded by the pocket periphery laminate material. In some forms, the pocket periphery laminate material can have an inner perimeter and the product can have at least one drainage opening for draining liquid from the pocket. The at least one drainage opening can include at least one opening in the first wall material or the second wall material occurring within 3 mm of the inner perimeter of the pocket periphery laminate material (and preferably a plurality of such openings) and/or at least one tunnel drain opening extending through the pocket periphery laminate material (and preferably a plurality of such tunnel drain openings). In addition or alternatively, (i) the pocket periphery laminate material can include collapsed pore structures of the first segment of the first wall material and the first segment of the second wall material; (ii) the first segment of the first wall material can have an average density greater than that of the second segment of the first wall material and the first segment of the second wall material can have an average density greater than that of the second segment of the second wall material; (iii) the first segment of the first wall material can have an average porosity greater than that of the second segment of the first wall material and the first segment of the second wall material can have an average density greater than that of the second segment of the second wall material; and/or (iv) the first segment of the first wall material can have an average thickness less than that of the second segment of the first wall material and the first segment of the second wall material can have an average thickness less than that of the second segment of the second wall material.

Additional embodiments provide an implantable pouch product as described in this Summary above or elsewhere herein, and an implantable medical device received (partially or completely) in the pocket of the implantable pouch product. The medical device can, in some embodiments, be an electronic medical device, for example a cardiac pacemaker or defibrillator device. Further embodiments provide methods of treating human or other animal patients that comprise implanting in the patient an implantable pouch product as described herein, typically containing an electronic medical device such as any of those described herein.

Another embodiment provides a method for making an implantable pouch product. The method includes provide providing a first wall material and a second wall material. The method further includes laminating a first segment of the first wall material to a first segment of the second wall material to define a pouch periphery laminate material. The laminating is conducted so as to leave a pocket defined by a second segment of the first wall material and a second segment of the second wall material that are not laminated to one another, the pocket being bounded by the pouch periphery laminate material. In some forms, the laminating can include providing a compressed construct having the first segment of the first wall material, in wetted condition, compressed against the first segment of the second wall material in wetted condition, freezing the compressed construct, and drying the compressed construct by lyophilization. Additionally or alternatively, the method can include cutting a plurality of openings in the second segment of the first wall material and/or in the second segment of the second wall material.

It will be understood that the product and method embodiments disclosed in this Summary above can include additional individual features, or combinations of features, as disclosed in connection with the embodiments in the Detailed Description below.

Other objects, embodiments, forms, features, advantages, aspects, and benefits shall become apparent from the detailed description and drawings included herein.

BRIEF DESCRIPTION OF THE DRAWINGS

FIG. 1A provides a side view of one embodiment of an implantable pouch product.

FIG. 2A provides a side view of another embodiment of an implantable pouch product.

FIG. 2B provides a right-end view of the implantable pouch product of FIG. 2A.

FIG. 2C provides a bottom-end view of the implantable pouch product of FIG. 2A.

FIG. 4A provides a side view of another embodiment of an implantable pouch product.

FIG. 4B provides a cross-sectional view of the implantable pouch product of FIG. 4A taken along line 4B-4B and viewed in the direction of the arrows.

DETAILED DESCRIPTION

Figure 1B:
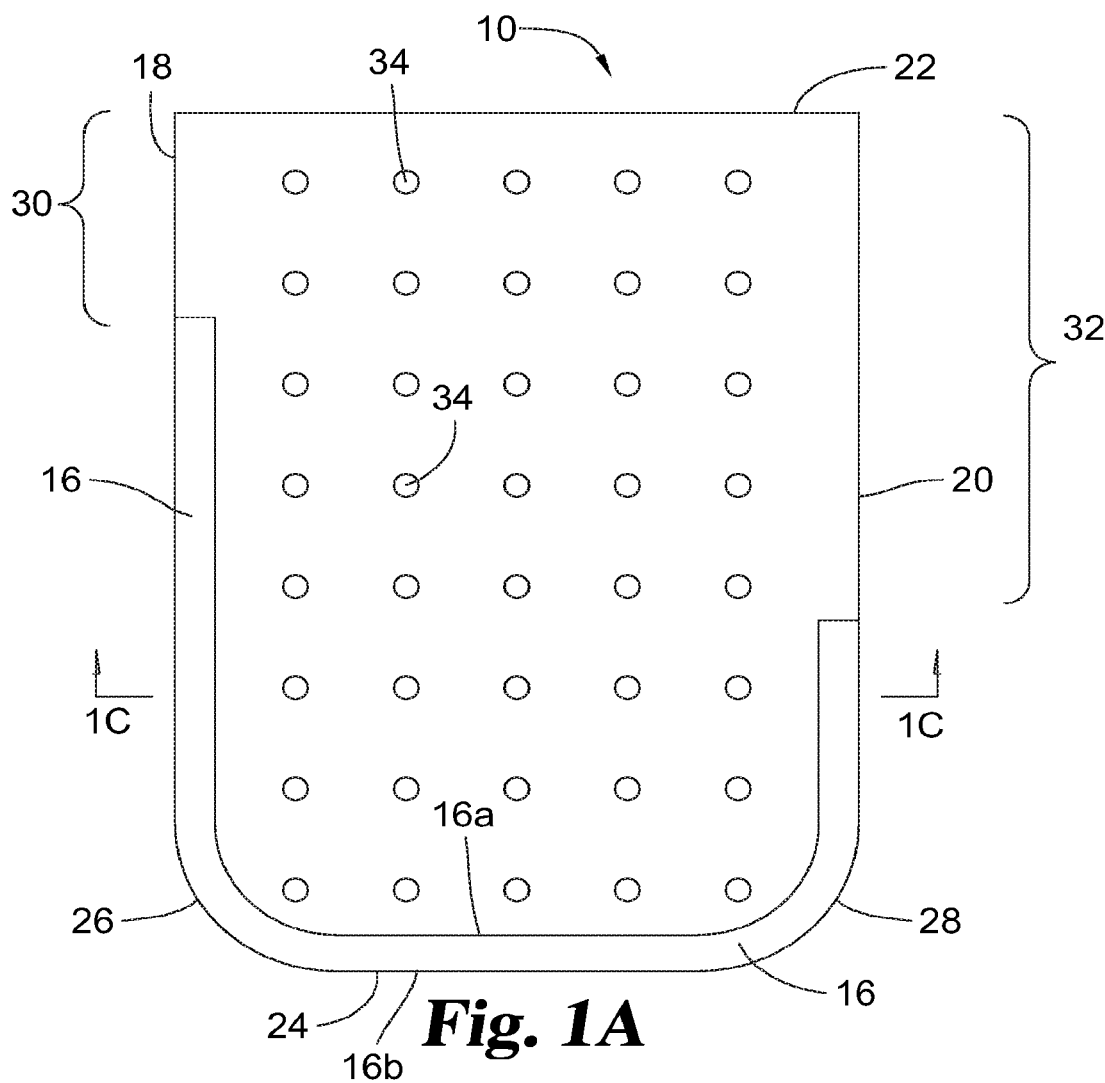
FIG. 1B provides a top end view of the implantable pouch product of FIG. 1A.
Figure 1B:
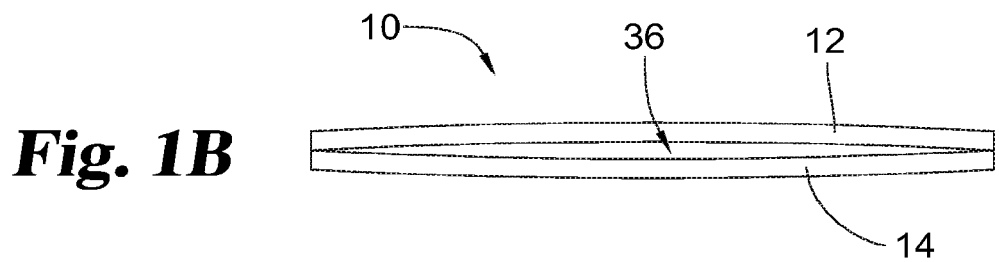

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, certain aspects herein relate to implantable pouch products having pockets bounded by laminated regions of first and second wall materials, and to related methods of production and use.

Figure 1C:
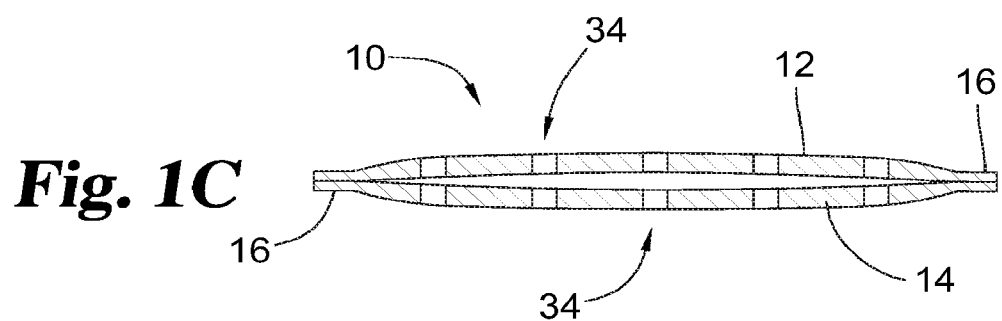
FIG. 1C provides a cross-sectional view of the implantable pouch product of FIG. 1A taken along line 1C-1C and viewed in the direction of the arrows.

With reference now to FIGS. 1A, 1B, and 1C, illustrated is one embodiment of a pouch product in accordance with the present disclosure. Pouch product 10 has a first wall 12 and second wall 14 that form a pocket therebetween. Walls 12 and 14 are bonded to one another along a peripheral flange 16 or pocket periphery laminate material, which provides a laminate material defining a periphery of the pocket of the pouch product 10. Pouch product 10 generally includes a first lateral side 18 and a second lateral side 20 opposed thereto. Pouch product 10 further includes a top side 22 and bottom side 24 opposed thereto. Lateral side 18 transitions to bottom side 24 through a rounded corner 28. Lateral side 20 transitions to bottom 24 through a rounded corner 26. In the illustrated embodiment the peripheral flange 16 does not extend entirely the distance from bottom side 24 to top side 22, but rather terminates along lateral side 18 a distance 30 from the top side 22. In similar fashion, flange 16 does not extend entirely from bottom side 24 to top side 22 as it extends along lateral side 20 of pouch product 10. Rather, flange 16 terminates along lateral side 20 a distance 32 from top side 22 of pouch product 10. In this fashion, both along lateral side 18 and along lateral 20, the walls 12 and 14 remain unbonded to one another for a distance (e.g. 30 or 32), creating upper flaps that can be separated by a user along top side 22 of pouch product 10 and for a distance along lateral sides 18 and 20 of pouch product 10. This may, for example, facilitate opening the pouch product to insert a device within the pocket, as discussed further hereinbelow. Distance 32 can in some embodiments be greater than distance 30, for example at least about 10% greater. Pouch product 10 also has a plurality of openings 34 defined in wall 12 as well a plurality of through openings 34 defined in wall 14. These openings allow fluid communication between the exterior of pouch product 10 and the inner pocket defined between walls 12 and 14, for example to facilitate passage of bodily liquids into and out of the inner pocket of pouch product 10 after implantation. Pouch product 10 of the illustrated embodiment shows one preferred arrangement for the openings 34 in which at least one and preferably a plurality of the openings 34 are spaced very closely to the inner perimeter 16a of the flange where it extends along the bottom side 24 of the pouch product 10, for example within about 3 mm of the inner perimeter 16a, more preferably within about 2 mm, and even more preferably within about 1 mm. Additionally or alternatively, at least one of and in some forms a plurality of openings 34 can intersect with the inner perimeter 16a of the flange 16 where it extends along the bottom side 24 of the pouch product 10. In this fashion, for uses in which pouch product 10 is implanted with bottom side 24 positioned lowermost in the patient, gravity-facilitated drains from the inner pocket defined between walls 12 and 14 are provided.

Figure 1D:
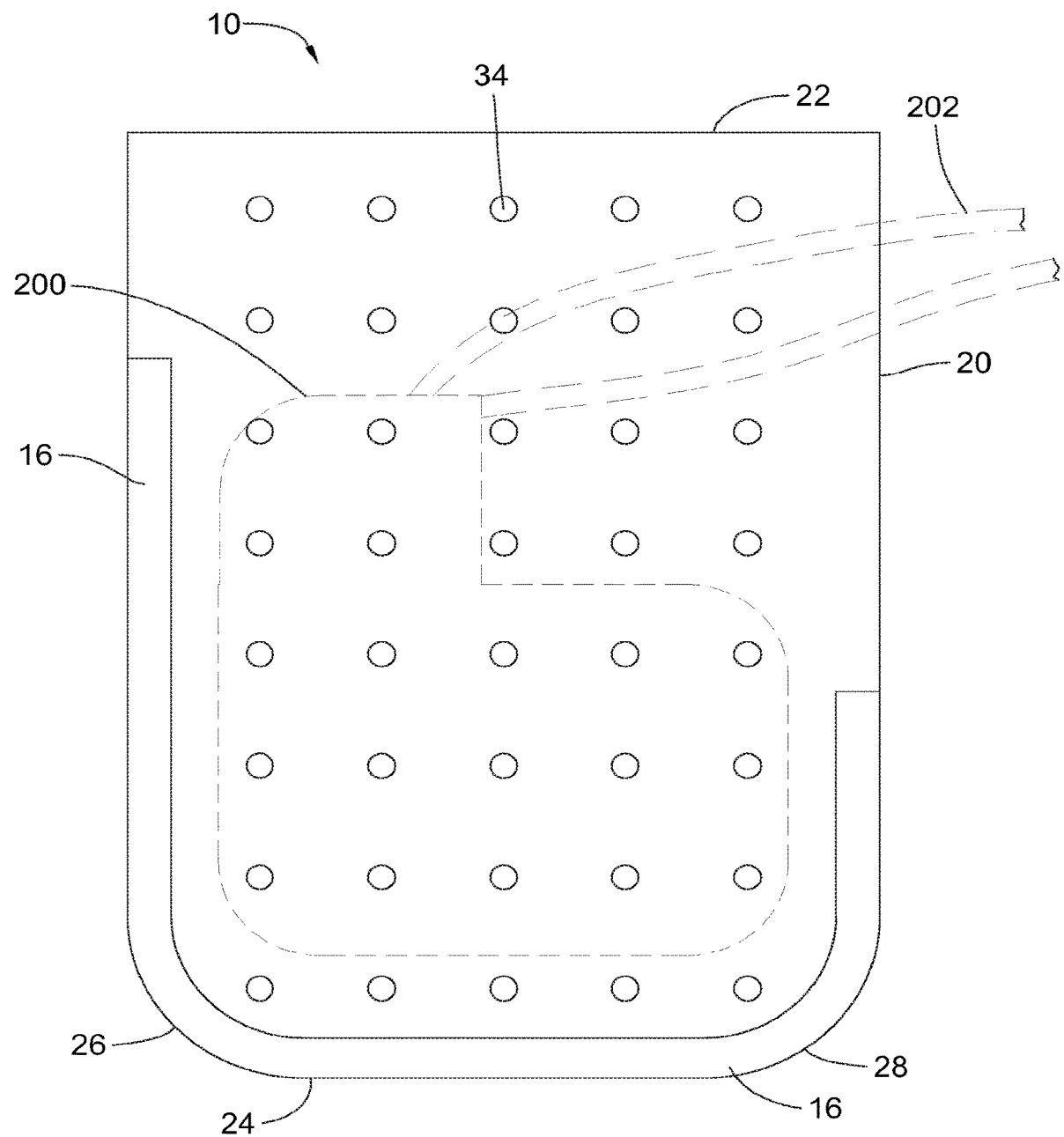
FIG. 1D provides a side view of the embodiment of an implantable pouch depicted in FIG. 1A having received therein a medical device.

As best shown in FIG. 1C, the material forming walls 12 and 14 is compressed to a thinner dimension in the areas of the bonded flange 16. Thus, generally, the material of walls 12 and 14 can be thicker, less dense, and/or more porous in regions other than flange 16 than within the region of flange 16. In certain embodiments, the material of walls 12 and 14 in the region of flange 16 is at least 10% denser, thinner, and/or less porous, than in regions other than flange 16. This difference or these differences in density, thickness and/or porosity can be observed by observing corresponding average differences, which can be determined using appropriate sampling of the subject regions and known testing methods for density, thickness and/or porosity. More preferably, the material of walls 12 and 14 in the region of flange 16 is at least 20%, at least 30%, at least 40%, or at least 50% denser, thinner, or less porous, on average, than in regions other than flange 16 and in particular in the regions of walls 12 and 14 that are not laminated to one another and define the pocket of the pouch product 10 for receiving therein a medical device. To achieve this, the flange 16 can be formed by bonding walls 12 and 14 to one another to form flange 16, with such bonding occurring under conditions that include compressing the material of walls 12 and 14 in the region of flange 16. During such compression bonding, the regions of walls 12 and 14 other than flange 16 can remain uncompressed or under less compression than the material in the region of flange 16. In this regard, the term "uncompressed" as used herein denotes that the material is not captured and forcibly compressed between two surfaces, and is not intended to exclude exposure of the material to the forces of gravity. In certain embodiments, flange 16 will have an average width from an inner perimeter 16a to an outer perimeter 16b of at least about 1 mm, or at least about 2 mm, and in some forms in the range of about 1 mm to about 2 cm or about 2 mm to about 1.5 cm. Additionally, in preferred forms of pouch product 10, and of other pouch products described herein, walls 12 and 14 are each themselves formed from or include a plurality of layers of one or more sheet form materials, desirably decellularized membranous tissue segments as described further hereinbelow. Pouch product 10 also includes an upper opening 36 through which a device may be inserted into the inner pocket formed between walls 12 and 14. In this regard, shown in FIG. 1D is a depiction of the implantable pouch product of FIG. 1A showing, in phantom, a medical device 200 received therein. The medical device 200 can be an electronic medical device in some embodiments (e.g. as described hereinbelow) and can be electrically connected to an electric lead or leads 202 that can extend from device 200 and, in use, have lead portion(s) that exit pouch product 10 and terminate in lead ends implanted at a location (e.g. within a wall of the heart) to receive electrical stimulation originating from device 200. It will be understood that medical device 200 and when present at least a portion of electric lead or leads 200 can also be received within the pockets of other pouch products described herein.

FIGS. 2A, 2B and 2C illustrate another embodiment of a pouch product of the present disclosure. Pouch product 40 can have features similar to those of pouch product 10 discussed above in connection with FIGS. 1A, 1B and 1C, unless noted otherwise. Similar elements are given similar numbers. Pouch product 40 has features additional to those of pouch product 10. In particular, pouch product 40 has an upper flap 42 formed by a section of wall 12 that extends beyond the top edge of wall 14. Flap 42 can, after inserting a medical device into pouch 40, be folded downward and over and against the exterior surface of wall 14, to close the opening 36 to the pocket within pouch product 40. To cause predictable folding, pouch product 40 can include a fold line 44 at which the material of wall 12 differs from adjacent material on either side of fold line 44, for example with fold line 44 forming a crease or being denser (e.g. formed by compression and drying) than adjacent material on either side of fold line 44. Pouch product 40 also includes reinforcement materials 46 and 48, such as sutures in the form of stitches, staples, rivets, or other materials that can be attached to and extend partly or completely through wall materials 12 and 14. Reinforcement materials 46 and 48 can be attached to walls 12 and 14 at positions at or proximate to the termini of flange 16 that occur at lateral sides 18 and 20 of the pouch product 40. The reinforcement materials can be located within the flange 16 region at these locations, outside of the flange 16 but adjacent the termini of the flange 16 region at these locations (e.g. above the flange termini on the lateral sides 18 and 20 in FIG. 2A) but preferably within about 3 mm of the termini or within about 2 mm of the termini, or can span the transition between the flange 16 region and adjacent non-flange regions. The reinforcement materials 46 and 48 can provide reinforcement against any undesired delamination of the flange 16 material that might occur as a user manipulates the upper regions of walls 12 and 14 to widen the opening 36 for insertion of a medical device or during other manipulations. The reinforcement materials can comprise or be constituted of a synthetic polymeric material, for example any of those described hereinbelow. Pouch product 40 also includes tunnel drains 50 located in the flange 16 occurring along the bottom side 24 of the pouch product. Tunnel drains 50 are bounded by flange material 16 and define lumens that provide fluid communication from the inner pocket of pouch 40 defined between walls 12 and 14 and the exterior of the pouch product 40, so that any liquid that passes into in the pocket can drain out of the pouch product 40 through tunnel drains 50.

Figure 3A:
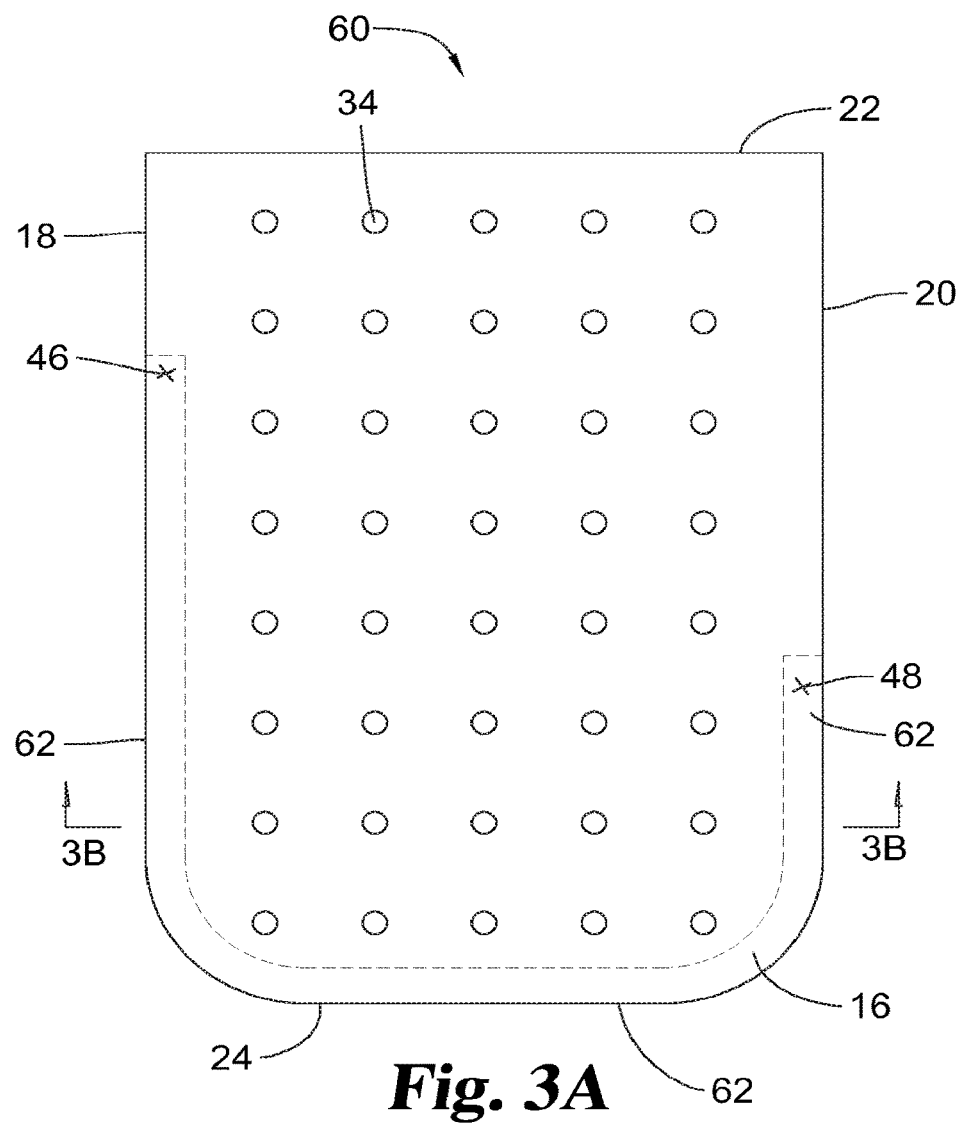
FIG. 3A provides a side view of another embodiment of an implantable pouch product.
Figure 3B:
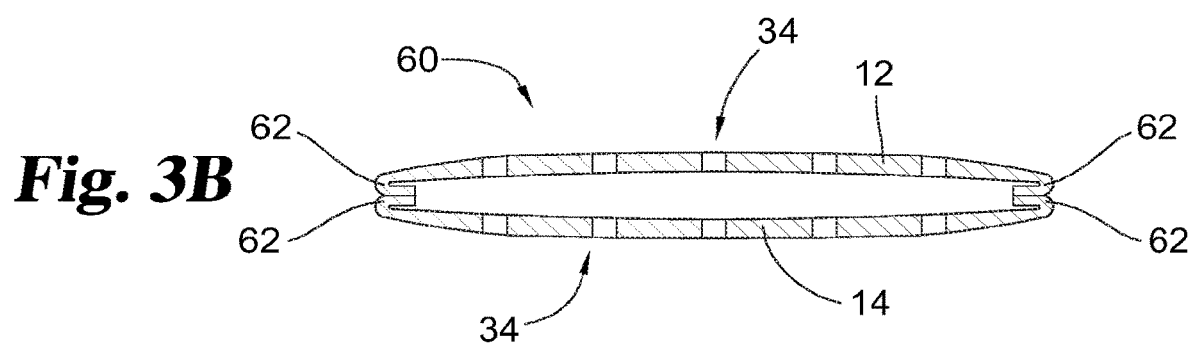
FIG. 3B provides a cross-sectional view of the implantable pouch product of FIG. 3A taken along line 3B-3B and viewed in the direction of the arrows.

FIGS. 3A and 3B illustrate another embodiment of a pouch product of the present disclosure. Pouch product 60 can have features similar to those of pouch product 10 discussed above in connection with FIGS. 1A, 1B and 1C or pouch product 40 discussed in connection with FIGS. 2A, 2B and 2C, unless noted otherwise. Pouch product 60 has a bonded flange 16 that extends inward from the outer periphery of the inner pocket, e.g. inward of the lateral sides 18 and 20 and bottom side 24, and thereby extends into the inner pocket defined between walls 12 and 14. The sides 18, 20 and 24 in the regions of the flange 16 are thus defined by curved or folded portions 62 of material of walls 12 and 14 where such material reverses direction. Curved or folded portions 62, which define the outermost edge of sides 18, 20 and 24 in the regions co-extensive with flange 16, can thereby be comprised of non-flange-16 material, which can as discussed above and elsewhere herein be more flexible, less dense, and/or more porous than the material of flange 16. This can, in some aspects, provide more advantageous properties to the sides 18, 20 and 24 of pouch product 60. It is preferred that curved or folded portions 62 have shape memory for their curved or folded shape, for example as can be imparted by drying them in their curved or folded condition. Curved or folded portions 62 with such shape memory can be adapted to maintain a substantially flat profile to the pouch product 60. Pouch product 60 or other pouch products having an interior-directed bonded flange of laminated material can in some forms be manufactured by initially forming a pouch product with an outwardly-directed flange of laminated material (e.g. as in FIGS. 1A, 1B, 1C and FIGS. 2A, 2B and 2C) and then inverting the formed product to locate the flange of laminated material interiorly into the pocket or inward of the outer periphery of the pocket. If needed or desired, after the inversion operation, the product can be partially or fully wetted and then re-dried to impart shape memory to the curved portions 62 as discussed above and/or to other regions of the pouch product. Alternatively, if such shape memory is desired, the inversion operation can be conducted with the material of walls 12 and 14 partially or fully wet, and then a drying operation can impart a new shape memory to curved portions 62 and/or other regions of the pouch product. In still other modes of manufacture, the flange 16 of laminated material can be initially formed in an inwardly-directed condition.

Referring now to FIGS. 4A and 4B, shown is another embodiment of a pouch product. Pouch product 70 can have features similar to those of pouch product 10 discussed above in connection with FIGS. 1A, 1B and 1C or pouch product 40 discussed in connection with FIGS. 2A, 2B and 2C, unless noted otherwise. Pouch product 70 has a bonded flange 16 like products 10 and 40, except product 70 also has an outer flange 72 of material occurring outward of (toward the periphery of product 70) flange 16. Outer flange 72 can, like other non-flange 16-material of pouch 70, be comprised of material of walls 12 and 14 that is more flexible, less dense, and/or more porous than the material of flange 16, as discussed above for materials other than flange 16. Outer flange 72 can thereby in some embodiments present an outermost edge of product 70 that is softer or less rigid (at least in a dry state) than that which would occur if flange 16 formed the outermost edge. For example, in some forms flange 16 can be formed by compressing and drying the walls 12 and 14 in the region of flange, while drying the walls 12 and 14 in the region of outer flange with no compression or less compression than that applied in forming the bonded flange 16. The material of walls 12 and 14 in the outer flange 72 region can be bonded to one another, or can be not bonded to one another, or combinations thereof in varied portions of the outer flange 72.

Figure 5:
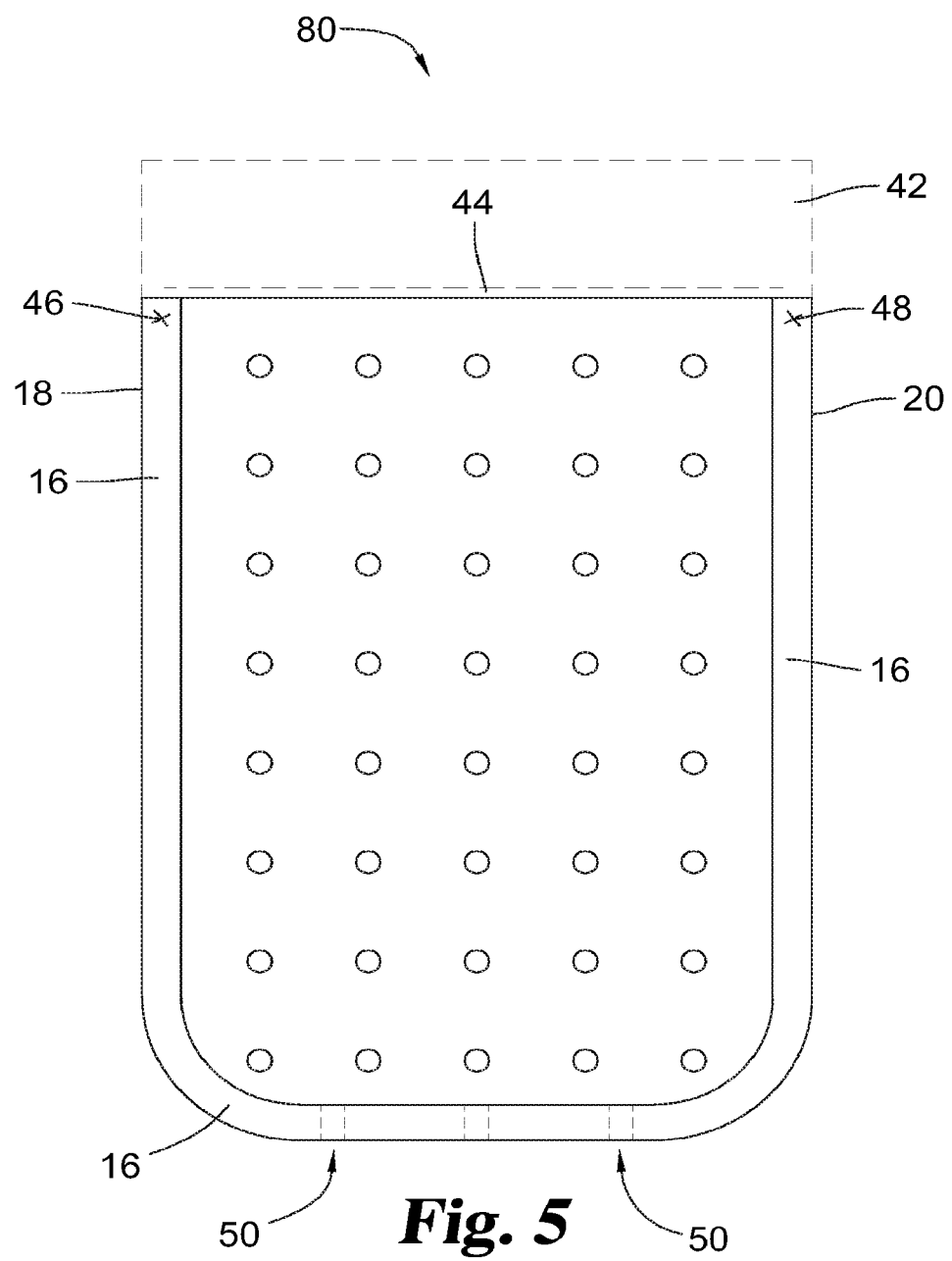
FIG. 5 provides a cross-sectional view of another embodiment of an implantable pouch product.

With reference to FIG. 5, shown is another embodiment of a pouch product. Pouch product 80 can have features similar to those of pouch product 10, 40, 60 or 70 discussed above, unless noted otherwise. Pouch product 80 has flange 16 that extends along sides 18 and 20 completely or essentially completely (within about 2 mm) to opening 36 occurring between walls 12 and 14. Pouch product 80 also optionally includes a flap 42 (shown in phantom) and fold line 44 as discussed in conjunction with product 40 depicted in FIGS. 2A, 2B and 2C above.

Figures 6A, 6B:
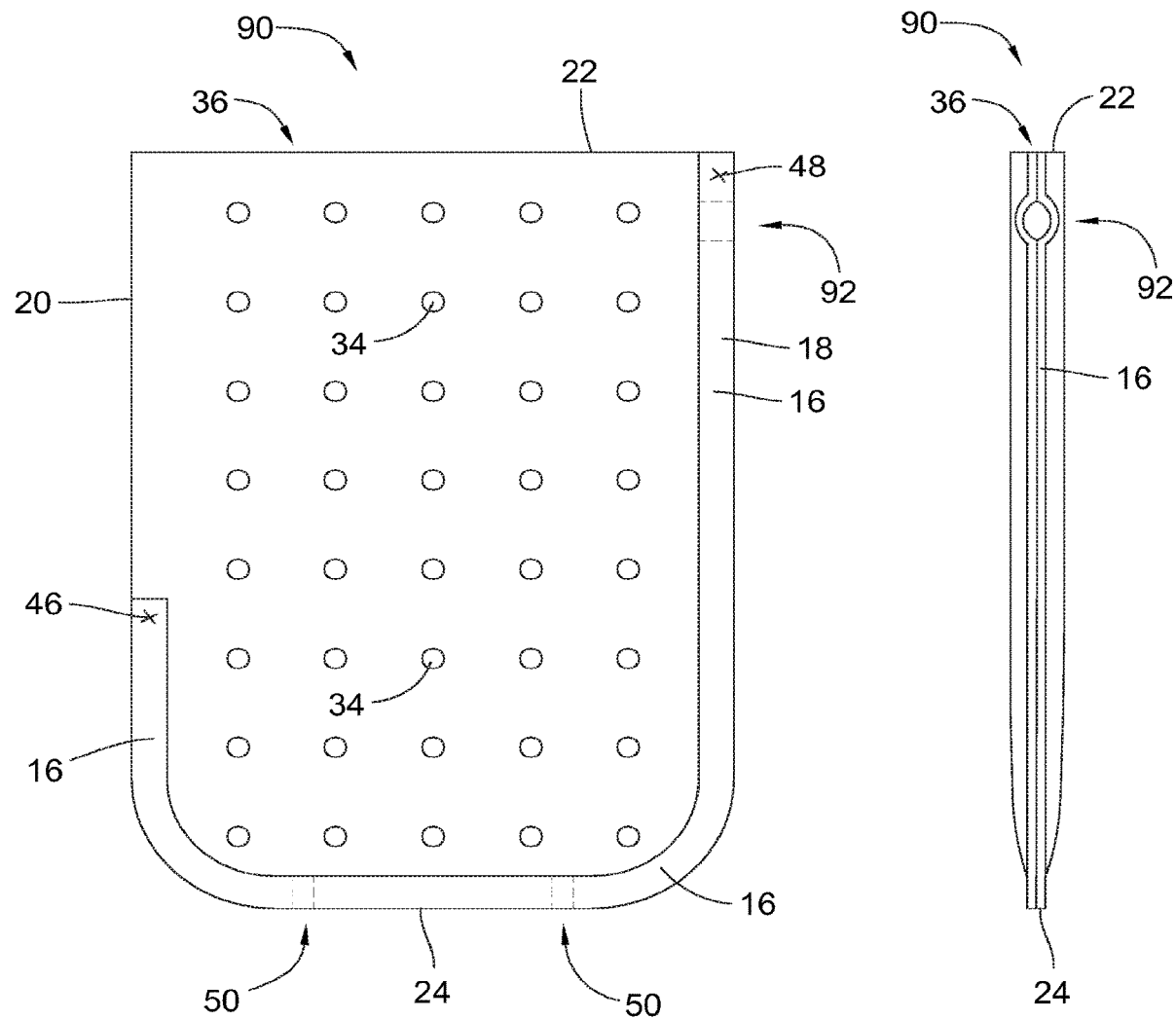
FIG. 6A provides a side view of another embodiment of an implantable pouch product.
FIG. 6B provides a right-end view of the implantable pouch product of FIG. 6A.
Figure 7A:
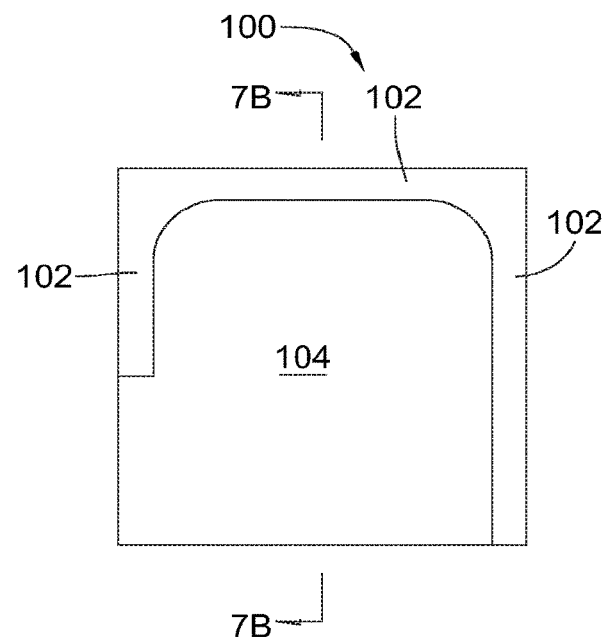
FIG. 7A provides a top view of one embodiment of a press mold that can be used to manufacture implantable pouch products.
Figure 7B:
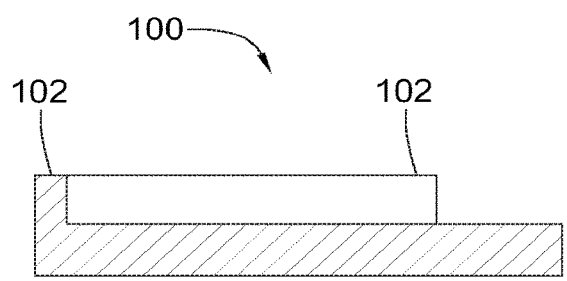
FIG. 7B provides a cross-sectional view of the press mold of FIG. 7A taken along line 7B-7B and viewed in the direction of the arrows.
Figure 7C:
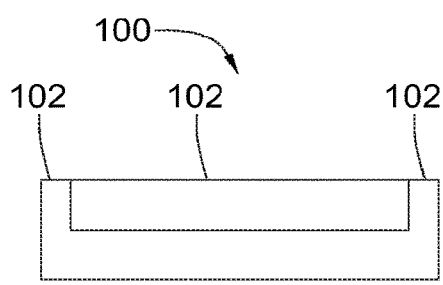
FIG. 7C provides a bottom end view of the press mold of FIG. 7A.
Figure 7D:
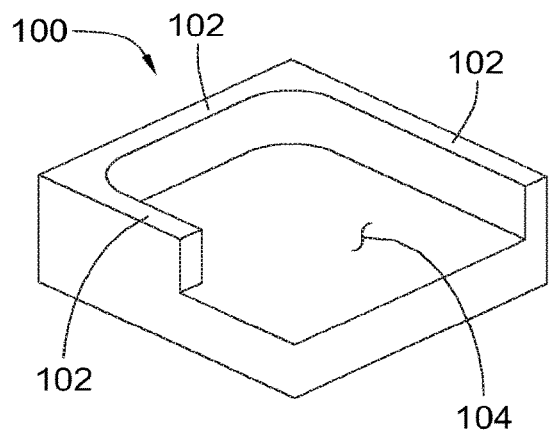
FIG. 7D provides a perspective view of the press mold of FIG. 7A.

FIGS. 6A and 6B illustrate another embodiment of a pouch product. Pouch product 90 can have features similar to those of pouch product 10, 40, 60, 70 or 80 discussed above, unless noted otherwise. Bonded flange 16 extending along side 18 has defined therein a lumen 92 bounded by laminated material of flange 16, through which one or more lead wires (e.g. lead(s) 202 of FIG. 1D) connected to a medical device (e.g. device 200 of FIG. 1D) received in the pocket of pouch 92 can extend from the interior to the exterior of pouch product 90. Flange 16 along side 18 can extend further toward opening 36 than flange 16 along side 20. In this manner, as discussed above, an upper flap can be created at the intersection of lateral side 20 and top side 22 of pouch 90, which can ease manipulation of the product to open opening 36. In one mode of use, the end of a lead extending from a patient can be passed through lumen 92 and out of opening 36. The lead can then be connected to an electronic medical device such as a pacemaker or defibrillator device, and the device then inserted through the opening 36 and into the pocket of pouch product 90.

FIGS. 7A, 7B, 7C and 7D depict various views of an illustrative press mold 100 that can be used in the manufacture of a segmentally laminated pouch product, for example a product with a lamination pattern as depicted in FIGS. 1 to 4. Press mold 100 defines a raised compression surface 102 in the pattern desired for flange 16. Compression surface 102 in use will create the lamination pattern of flange 16 or a lamination pattern that upon modification, for example by trimming away excess laminated portions, can create the lamination pattern of flange 16. Press mold 100 also defines a pocket space 104 occurring interiorly of raised compression surface 102, so that material to respective create walls 12 and 14 or portions thereof that is positioned within pocket space will remain unlaminated during use of mold and thereby create a pocket within the pouch products manufactured.

Figure 8A:
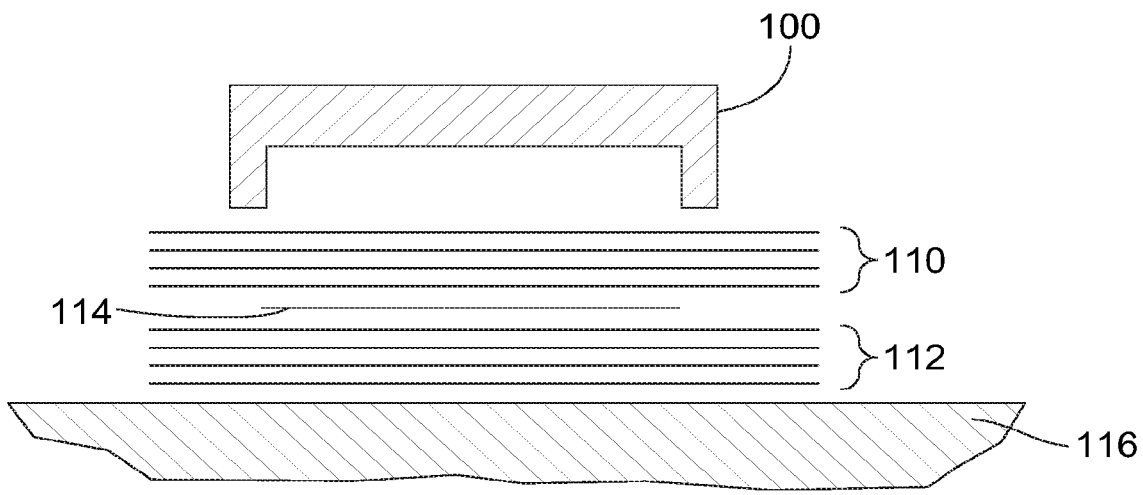
FIG. 8A provides a cross-sectional view depicting the press mold of FIGS. 7A to 7D in use in the manufacture of an implantable pouch product.
Figure 8B:
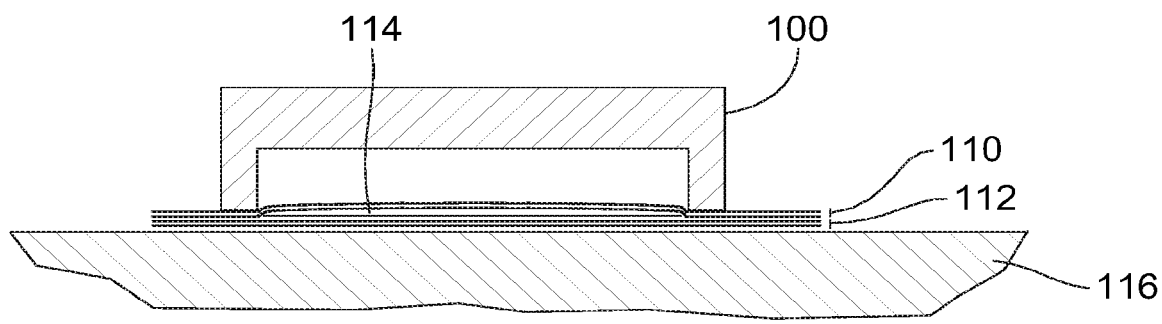
FIG. 8B provides a cross-sectional view depicting the press mold of FIGS. 7A to 7D in use in a compression stage of the manufacture of an implantable pouch product.

FIGS. 8A and 8B depict one illustrative use of press mold 100 in the manufacture of a pouch product. In FIG. 8A, a first sheet or plurality of sheets 110 of material (e.g. any of those materials described herein, which can be wet with a liquid such as an aqueous liquid) and a second sheet or plurality of sheets 112 of material (e.g. any of those described herein, which can be wet with a liquid such as an aqueous liquid) are provided, and a separating sheet or sheets 114 (e.g. made out of a relatively non-stick polymeric sheet material such as polytetrafluoroethylene or Tyvek® (polyethylene polymer film)) is/are positioned between portions of sheet or sheets 110 and sheet or sheets 112 in the pocket area of walls 12 and 14 not to be laminated to one another (e.g. located in alignment of pocket space 104 of press mold 100). This layup construct including mold 100, sheet or sheets 110 and 112, and separating sheet/sheets 114 can be provided on a compression surface 116. Thereafter, as shown in FIG. 8B, the components of the layup construct can be compressed (e.g. clamped) against compression surface 116. The components of the layup construct can then be subjected to drying conditions, for example by first freezing the layup construct and then subjecting the frozen layup construct to lyophilization conditions, to segmentally laminate the materials 110 and 112 for walls 12 and 14 to create the pouch product or a precursor that can be modified (e.g. trimmed and/or locally reinforced as described herein) to provide the pouch product. When a layup construct such as that depicted in FIG. 8B is subjected to freezing and then lyophilization conditions, the compressed material in the region of flange 16 will be laminated to form a laminate material periphery for the pouch product as described herein. When a plurality of sheets 110 and a plurality of sheets 112 are used to create walls 12 and 14, the sheets 110 can also laminate to one another in non-compressed regions and the sheets 110 and 112 can also laminate to one another in non-compressed regions, to form laminate walls 12 and 14 occurring on either side of the interior pocket of the formed pouch device. This lamination in the formation of laminate walls 12 and 14 can occur due to contact of the wet sheets 110 with one another and contact of the wet sheets 112 with one another during freezing and then lyophilization of the layup construct. In such cases, the presence of the separation layer or layers 114 can prevent lamination of the walls 12 and 14 to one another to provide the interior space for the pouch product. After the drying, the separation layer or layers 114 can be removed. The dried pouch product can then be further processed, e.g. by stamping or otherwise cutting to create openings 34, by trimming away any excess material, by introducing reinforcements, and other potential modifications. The finalized implantable product can then be packaged and sterilized as described herein.

It will be understood that while one illustrative press mold 100 has been depicted herein to provide certain embodiments of segmental lamination (e.g. as occur in pouch products depicted in FIGS. 1-4), similar press molds can also be designed and used to provide differing segmental lamination patterns in the manufacture of other pouch products, e.g. the products depicted in FIGS. 5 and 6 herein. Additionally, in some uses of press mold 100 or other molds in forming the segmentally laminated structures of the pouch products, a compressible material such as a porous foam sheet can be positioned between the material of wall(s) 12 and/or 14 and the compression surface(s) of the mold and/or the compression surface (e.g. 116) against which the mold is used. Such a compressible sheet material can facilitate additional conformance of the compression surface to the material(s) 12 and/or 14, and can be removed and potentially discarded after use during the compression and lamination processing. Given the disclosures herein the manufacture and use of these or other press molds, including one-part or multi-part (e.g. 2-part) molds, and the use of still other techniques to make the segmental lamination patterns disclosed herein, will be within the purview of those of ordinary skill in the field.

In certain embodiments, the implantable pouch product can have at least a portion, and in typical forms only a portion, of its outer periphery defined by a fold occurring between the first (e.g. front) wall of the pouch product and the second (e.g. back) wall of the pouch product. In these embodiments, a single piece of wall material can be folded to provide the fold and the first and second walls of the pouch product (or at least portions thereof). The single piece of wall material can be a single layer wall material or a laminate wall material, for example any of the laminate wall materials described herein. In some embodiments about 5% to about 70% of the total length of the outer periphery of the pouch product is defined by such a fold, more typically about 10% to about 50%. The bonded flange (e.g. 16 or 126 herein) can be positioned inward of the fold, for example beginning at the fold and extending inward thereof or beginning inward of the fold and extending a distance further inward. In this manner, should the bonded flange experience separation of the bonded layers of the flange (e.g. after implantation), the fold will nonetheless provide protection against escape of the device or contents of the implantable pouch products. Illustratively, in the manufacture of the implantable pouch products shown in FIGS. 1-6, rather than the front and back walls of the pouches being made from separate sheets of material, the front and back walls can be made from a single sheet or piece of material that has a fold between the front and back walls. The fold can, for example, provide the outermost periphery of the bottom sides 24 of the pouch products of FIGS. 1-6. In other embodiments, the fold The implantable pouches can be implanted with bottom sides occurring in a lowermost position of the human or other patient when in a standing position, so that the fold line can protect against escape of the device or other contents within the pouch should the bonded flange experience separation of its layers, e.g. caused at least in part by the weight of the device or contents under gravity or during accelerative movements of the patient such as walking, running or jumping.

Figure 10A:
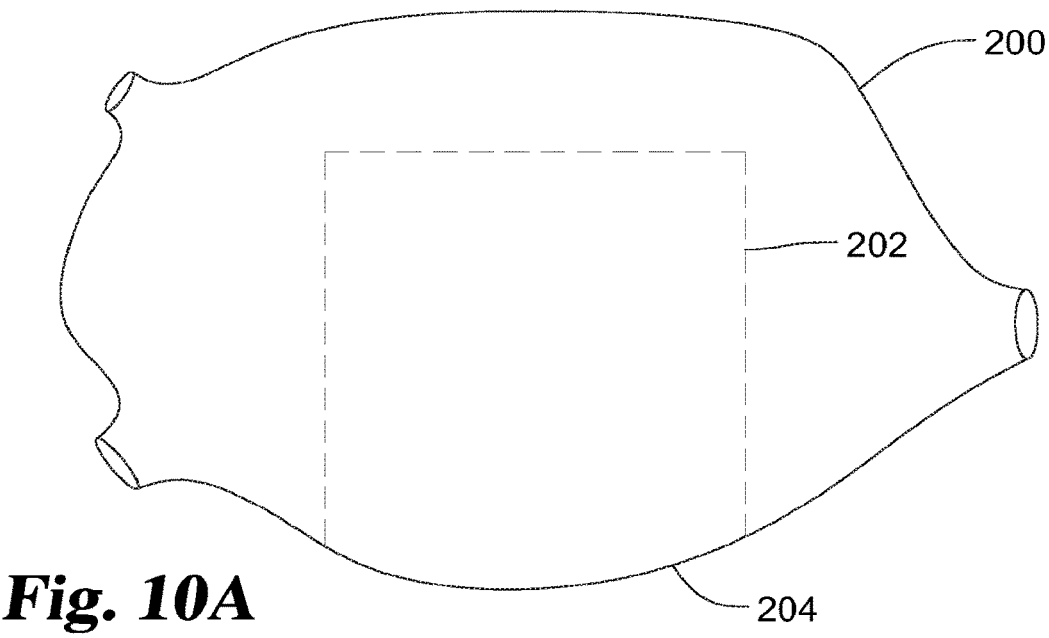
FIG. 10A shows a porcine bladder and cut lines (shown in dotted lines) used in the manufacture of one embodiment of an implantable pouch.
Figure 10B:
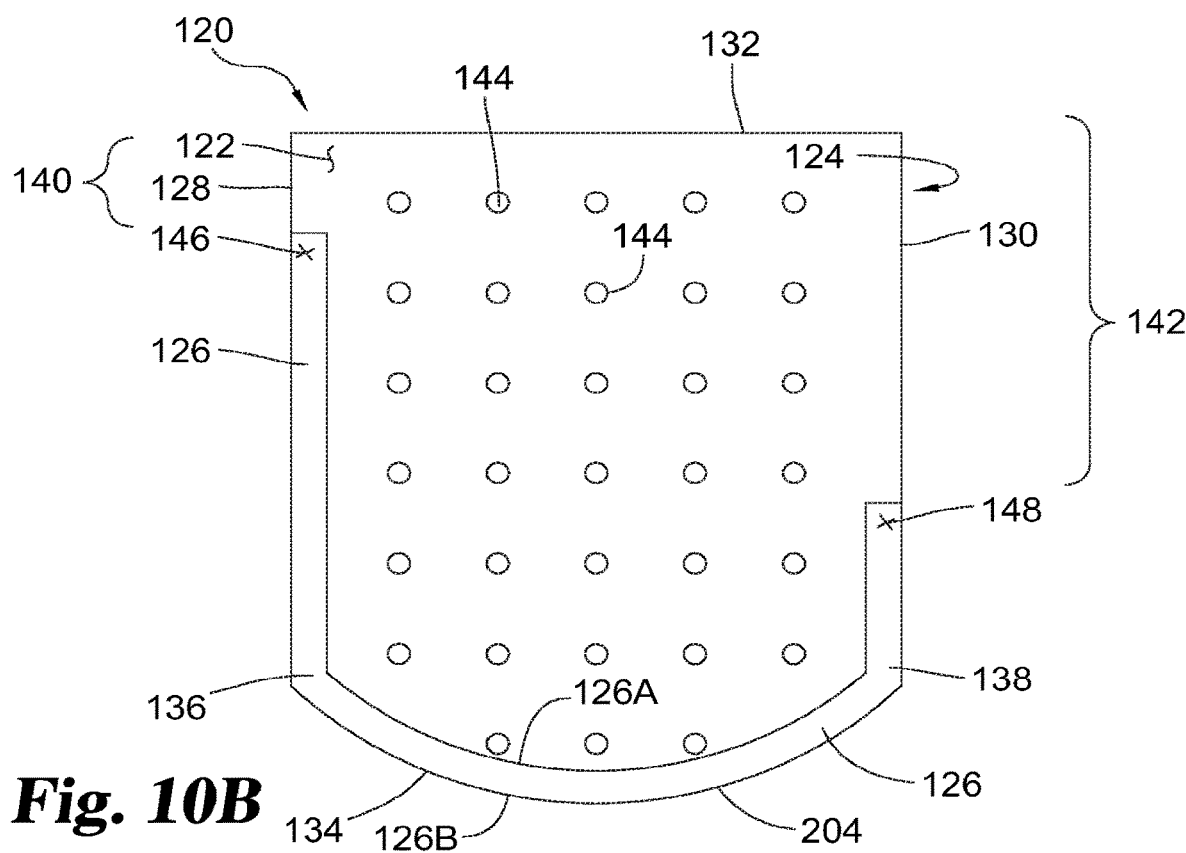
FIG. 10B provides a side view of an implantable pouch product made using the porcine bladder of FIG. 10A.

In certain embodiments, the implantable pouch products herein will be manufactured from decellularized membranous tissue segments and/or decellularized extracellular matrices obtained from a native tissue structure that has the form of a tube (e.g. intestine) or a chamber (e.g. urinary bladder or stomach). Such native tissue structures of an appropriate size for the pouch product to be manufactured can, for example, be isolated from adult or juvenile animals, and especially non-human mammals. Such native tissue structures naturally provide material for front and back walls of the pouch structures, with a fold in between that can be used to define at least a portion of the outer periphery of the pouch product as discussed above. As one illustration, with reference now to FIGS. 10A and 10B, FIG. 10A shows a porcine bladder (or other mammalian animal bladder) 200 and a cut line 202 thereon for cutting through the front and back walls of the bladder to isolate a segment of the bladder tissue to be used in the manufacture of an implantable pouch product 120. The bladder 200 has a natural chamber shape, providing a folded edge 204 occurring between front and back walls of the bladder to be used to make, respectively, front and back walls of the implantable pouch product 120 (or at least portions thereof). It will be understood that corresponding front and back walls and folded edges are provided by other tubular or chamber shaped tissues, e.g. those discussed above, which can be correspondingly used. As well, chamber tissue, such as urinary bladder tissue or stomach tissue, provides naturally curved folds (e.g. folded edge 204), typically convexly curved folds, which can form curved portions of outer peripheries of the manufactured implantable pouch products, e.g. wherein naturally convexly curved folds are used to form convexly curved portions of outer peripheries of the manufactured implantable pouch products. In doing so, the chamber shaped tissue can be stretched or otherwise deformed in the hydrated state in the manufacture of the implantable pouch product, to provide a uniform manufactured curve for the curved portion of the outer periphery, which can set to shape, e.g. to be consistent from product to product. The hydrated product having the manufactured curve can be dried and/or crosslinked, e.g. using any of those methods described herein, to provide shape memory to the manufactured curve. Presses, jigs, molds or other implements can be used in shaping and holding the manufactured curve, e.g. while it is set by drying and/or crosslinking to provide shape memory. In some embodiments, the implements are the same as those used in creating the bonded flange of the pouch product, for example, bonded flange 126 of pouch product 120.

With reference more particularly now to FIG. 10B, it will be understood that pouch 120 can have features corresponding to those of the pouch products described in conjunction with FIGS. 1-6, unless specified otherwise. Pouch product 120 has a first wall 122 and second wall 124 (opposite to wall 122, not visible) that form a pocket therebetween. Walls 122 and 124 are bonded to one another along a peripheral flange 126 or pocket periphery laminate material, which provides a laminate material defining a periphery of the pocket of the pouch product 120. Pouch product 120 generally includes a first lateral side 128 and a second lateral side 130 opposed thereto. Pouch product 120 further includes a top side 132 and curved bottom side 134 opposed thereto. Lateral side 128 transitions to bottom side 134 through a corner 138. Lateral side 130 transitions to curved bottom side 134 through a corner 136. In the illustrated embodiment the peripheral flange 126 does not extend entirely the distance from bottom side 134 to top side 132, but rather terminates along lateral side 128 a distance 140 from the top side 132. In similar fashion, flange 126 does not extend entirely from bottom side 134 to top side 132 as it extends along lateral side 130 of pouch product 120. Rather, flange 126 terminates along lateral side 130 a distance 142 from top side 132 of pouch product 120. In this fashion, both along lateral side 128 and along lateral 130, the walls 122 and 124 remain unbonded to one another for a distance (e.g. 140 or 142), creating upper flaps that can be separated by a user along top side 132 of pouch product 120 and for a distance along lateral sides 128 and 130 of pouch product 120. This may, for example, facilitate opening the pouch product to insert a device within the pocket, as discussed herein. Distance 142 can in some embodiments be greater than distance 140, for example at least about 10% greater. Pouch product 120 also has a plurality of openings 144 defined in wall 122 as well a plurality of through openings 34 defined in wall 124 (not shown). These openings allow fluid communication between the exterior of pouch product 120 and the inner pocket defined between walls 122 and 124, for example to facilitate passage of bodily liquids into and out of the inner pocket of pouch product 120 after implantation. Pouch product 120 of the illustrated embodiment shows one preferred arrangement for the openings '144 in which at least one and preferably a plurality of the openings 144 are spaced very closely to the inner perimeter 126A of the flange where it extends along the bottom side 134 of the pouch product 130, for example within about 3 mm of the inner perimeter 126A, more preferably within about 2 mm, and even more preferably within about 1 mm. Additionally or alternatively, at least one of and in some forms a plurality of openings 144 can intersect with the inner perimeter 126A of the flange 126 where it extends along the bottom side 134 of the pouch product 120. In this fashion, for uses in which pouch product 120 is implanted with bottom side 134 positioned lowermost in the patient, gravity-facilitated drains from the inner pocket defined between walls 122 and 124 are provided.

As with the pouch product embodiments described in conjunction with FIGS. 1-6, the material forming walls 122 and 124 can be compressed to a thinner dimension in the areas of the bonded flange 126. Thus, generally, the material of walls 122 and 124 can be thicker, less dense, and/or more porous in regions other than flange 126 than within the region of flange 126. In certain embodiments, the material of walls 122 and 124 in the region of flange 126 is at least 10% denser, thinner, and/or less porous, than in regions other than flange 126. This difference or these differences in density, thickness and/or porosity can be observed by observing corresponding average differences, which can be determined using appropriate sampling of the subject regions and known testing methods for density, thickness and/or porosity. More preferably, the material of walls 122 and 124 in the region of flange 126 is at least 20%, at least 30%, at least 40%, or at least 50% denser, thinner, or less porous, on average, than in regions other than flange 126 and in particular in the regions of walls 122 and 124 that are not laminated to one another and define the pocket of the pouch product 120 for receiving therein a medical device. To achieve this, the flange 126 can be formed by bonding walls 122 and 124 to one another to form flange 126, with such bonding occurring under conditions that include compressing the material of walls 122 and 124 in the region of flange 126. During such compression bonding, the regions of walls 122 and 124 other than flange 126 can remain uncompressed or under less compression than the material in the region of flange 126. In this regard, the term "uncompressed" as used herein denotes that the material is not captured and forcibly compressed between two surfaces, and is not intended to exclude exposure of the material to the forces of gravity. In certain embodiments, flange 126 will have an average width from an inner perimeter 126A to an outer perimeter 126B of at least about 1 mm, or at least about 2 mm, and in some forms in the range of about 1 mm to about 2 cm or about 2 mm to about 1.5 cm. Additionally, walls 122 and 124 can each themselves be formed from or include a plurality of layers of one or more sheet form materials, desirably decellularized membranous tissue segments as described further hereinbelow. In such a construction, different fold-containing segments of a urinary bladder, stomach or other chamber shaped tissue, or of multiple isolated chamber shaped tissues, can be used. As well, a fold-containing segment of such a chamber shaped tissue can be laminated in some or all areas with other sheet form material, e.g. other decellularized membranous sheet form tissue segments, to reinforce the fold-containing segment of the chamber shaped tissue.

Pouch product 120 also includes an upper opening through which a device may be inserted into the inner pocket formed between walls 122 and 124. For example, a medical device 200 as shown and described in conjunction with FIG. 1D can be inserted into the pocket of pouch 120. As before, the medical device 200 can be an electronic medical device in some embodiments (e.g. as described hereinbelow) and can be electrically connected to an electric lead or leads 202 that can extend from device 200 and, in use, have lead portion(s) that exit pouch product 120 and terminate in lead ends implanted at a location (e.g. within a wall of the heart) to receive electrical stimulation originating from device 200. It will be understood that medical device 200 and when present at least a portion of electric lead or leads 200 can also be received within the pockets of other pouch products described herein.

As with some other pouch products disclosed above, pouch product 120 in certain embodiments include reinforcement materials 146 and 148, such as sutures, stitches, staples, rivets, or other materials that can be attached to and extend partly or completely through wall materials 122 and 124. Reinforcement materials 146 and 148 can be attached to walls 122 and 124 at positions at or proximate to the termini of flange 126 that occur at lateral sides 128 and 130 of the pouch product 120. The reinforcement materials can be located within the flange 126 region at these locations, outside of the flange 126 but adjacent the termini of the flange 126 region at these locations (e.g. above the flange termini on the lateral sides 128 and 130) but preferably within about 3 mm of the termini or within about 2 mm of the termini, or can span the transition between the flange 126 region and adjacent non-flange regions. The reinforcement materials 146 and 148 can provide reinforcement against any undesired delamination of the flange 126 material that might occur as a user manipulates the upper regions of walls 122 and 124 to widen the opening of the pouch for insertion of a medical device or during other manipulations. The reinforcement materials can comprise or be constituted of a synthetic polymeric material, for example any of those described hereinbelow.

Figure 9A:
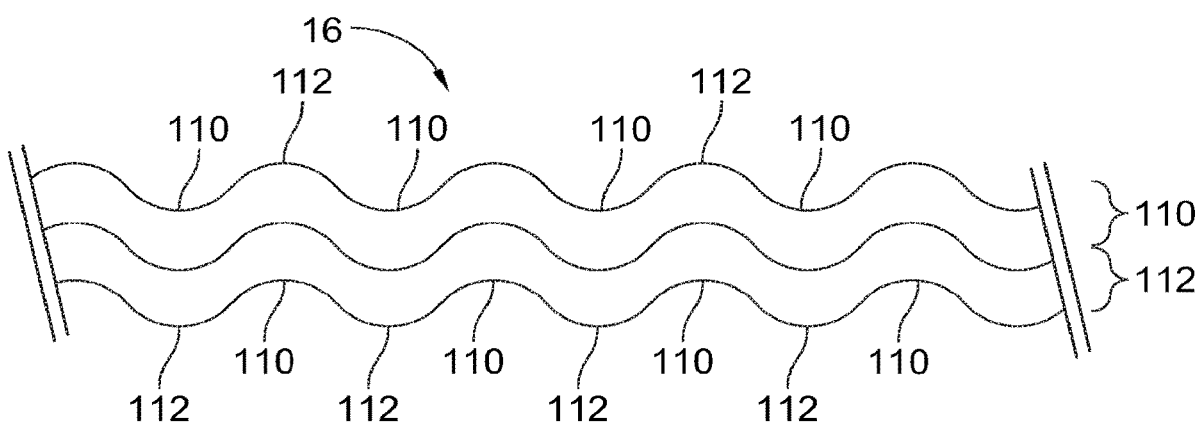
FIG. 9A provides a side view of a segment of one embodiment of an undulating flange material for an implantable pouch product.

While in the Figures discussed hereinabove the laminated flange 16 or 126 is depicted as a generally planar region of laminated material, in some beneficial embodiments, the laminated flange 16 or 126 can have a random or non-random pattern of undulations (e.g. corrugations). This random or non-random pattern of undulations can provide an increase in the surface area of laminated material interface per unit of linear length of the flange 16 or 126. The pattern of undulations can in some embodiments provide valleys of laminated material occurring between adjacent peaks of laminated material, wherein the peaks have a height of at least about 0.1 mm, or at least about 0.2 mm, relative to adjacent valleys, and typically within the range of about 0.1 mm to about 2 mm, or about 0.1 mm to about 1 mm, or about 0.1 mm to about 0.5 mm. In some forms, a compression surface of a press mold (e.g. 102) and/or a compression surface 116 used in conjunction with a press mold can define a corresponding random or non-random pattern of undulations so that upon compressive use to create a laminated flange 16, the flange 16 or 126 is patterned as described above. In these regards, FIG. 9A shows a side view of a segment of one embodiment of a flange region 16 having a pattern of undulations that includes valleys of laminated material 110 of walls 12 and 14 and peaks of laminated material 112 of walls 12 and 14. It will understood that such a flange region can be included for all or part of flange 16 of the embodiments depicted in FIGS. 1 to 6 herein as well as in other implantable pouch embodiments disclosed herein (e.g. that disclosed in FIG. 10B). Further, it will be understood that other patterns of undulation can be provided, for example in patterns providing a series of raised bumps or peaks (e.g. a spherical segment, conical or pyramidal shape) interspersed among similarly shaped indentations. In these or other undulating patterns, the peaks and valleys can have dimensions as described above in some forms.

In preferred uses, the pouch products, e.g. pouch products 10, 40, 60, 70, 80, 90, or 120 are used to receive therein an electronic medical device, such as a pacemaker or defibrillator device, or a neurostimulation device, and the combination of the pouch and device are then implanted in a human or non-human animal patient, for example subcutaneously. In human uses, the pocket and received medical device will often be planted subcutaneously in the chest of the patient. To secure the medical device within the pouch, one or more sutures can be passed through the walls 12 and/or 14 (or 122 and/or 124) of the pouch to hold it closed, and/or through tissue of the patient, to secure the pouch and device in place at the desired patient location. The skin of the patient can then be surgically closed over the subcutaneously or otherwise implanted pouch/device combination.

Turning now to a more detailed discussion of materials that can be utilized in making pouches of the present disclosure, particular advantage will be provided by pouch products that incorporate a remodelable material, especially where such a material is included in or constitutes wall 12 and/or wall 14 or wall 122 and/or wall 124. Such remodelable materials can be provided by a collagen-containing materials, e.g., provided in a reconstituted or non-reconstituted form, for example where the collagen has been obtained from a warm-blooded vertebrate, and especially a mammal. Isolated collagen-containing materials can be processed so as to have remodelable, angiogenic properties and promote cellular invasion and ingrowth, and in this regard, inventive constructs comprising a remodelable material and containing an electronic implantable medical device can be effective upon implantation to stimulate ingrowth of adjacent tissues into the construct such that the remodelable material gradually breaks down and becomes replaced by new patient tissue so that a new, remodeled tissue structure is generated forming a patient tissue pouch around the implantable medical device ("IMD") or other device or material. With such products, the functionality of the pocket is maintained throughout the remodeling process so that the IMD will continue to be surrounded by a functional and device-friendly pocket or pocket-like structure as the remodeling occurs.

Suitable remodelable materials can be provided by decellularized membranous tissue segments, which can be provided by collagenous extracellular matrix (ECM) materials. For example, suitable collagenous materials include ECM materials such as those comprising submucosa, renal capsule membrane, amnion, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. Collagenous matrices that are quite pliable so as to be easily conformable to the IMD will be useful in certain aspects of the invention. As well, as discussed above, in certain embodiments, the pouch products will incorporate a fold line-containing segment of a tubular (e.g. intestine) or chamber shaped (e.g. stomach or urinary bladder) native tissue; such native tissues can be decellularized to provide the decellularized membranous tissue segment prior to or after cutting the fold-line containing segment from the native tissue for use in constructing the pouch product, as discussed hereinabove. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Remodelable ECM tissue materials harvested as intact sheets from a mammalian source and processed to remove cellular debris advantageously retain at least a portion of and potentially all of the native collagen microarchitecture of the source extracellular matrix. This matrix of collagen fibers provides a scaffold to facilitate and support tissue ingrowth, particularly in bioactive ECM implant materials, such as porcine small intestinal submucosa or SIS (Surgisis® Biodesign™, Cook Medical, Bloomington Ind.), that are processed to retain an effective level of growth factors and other bioactive constituents from the source tissue. In this regard, when an inventive construct incorporates this sort of material, cells will invade the remodelable material upon implantation eventually leading to the generation of a newly-remodeled, functional tissue structure, for example, providing at least part of a pocket or pocket-like structure around a pacemaker or other implantable medical device (IMD). In some forms, the generated structure will provide a remodeled tissue wall that covers at least part of the medical device. Remodeled, organized tissue layers, when formed, can conform to an IMD to provide a secure, fitted placement of the IMD at the implant site.

Inventive pouch products that incorporate a remodelable and/or bioresorbable material can place the IMD in a device-friendly environment, for example, by generating a new, viable and functional tissue structure around the IMD. With persistent synthetic polymer products, the foreign body (i.e., the IMD or the non-degradable structure containing the IMD) can become encapsulated by rigid, fibrotic scar tissue which can be problematic for a number of reasons. For one, the rigid non-functional tissue and potentially deformations of anon-degradable containment structure can be irritating to the patient, and can otherwise be a source of discomfort and distraction. Also, this sort of rigid and uncontrolled fibrotic scar tissue can be much more difficult and dangerous to manage should the IMD ever need to be explanted or accessed for any reason.

With preferred remodelable pouch products, it is possible in some aspects to generate highly-functional and organized tissue structures around an IMD, to reduce the amount of total scar tissue occurring around the implant, to keep unremodeled encapsulating scar tissue from contacting the IMD, and/or to better predict and manage the type(s) of growth occurring in and/or around the implant and/or any components or accessories associated with the implant, among other things. In certain embodiments, it will be possible to temporarily access the generated remodeled patient tissue pouch or even replace an IMD without removing while leaving the remodeled pouch intact.

Continuing with a discussion of materials that can be utilized in embodiments of the present invention, when used, a submucosa-containing or other ECM tissue used in the invention is preferably highly purified, for example, as described in U.S. Pat. No. 6,206,931 to Cook et al. or in U.S. Pat. No. 8,192,763 of Cook Biotech Incorporated. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 and/or in U.S. Pat. No. 8,192,763 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source. As disclosed herein, in certain embodiments, wall materials for the pouch products will be provided by a laminate of multiple layers of submucosa-containing ECM material and/or other ECM material.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa-containing or other ECM materials, when used in a pouch product herein, can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive substances such as those synthetically produced by recombinant technology or other methods (e.g., genetic material such as DNA), may be incorporated into an ECM material. These non-native bioactive substances may be naturally-derived or recombinantly produced proteins that correspond to those natively occurring in an ECM tissue, but perhaps of a different species. These non-native bioactive substances may also be drug substances. Illustrative drug substances that may be added to materials include, for example, anti-clotting agents, e.g. heparin, antibiotics, statins, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient. In certain embodiments, one or more antibiotic agents will be incorporated into ECM material included in the pocket construct, for example rifampin, minocycline, or a combination thereof. Alternatively or in addition, rifampin, minocycline, a combination thereof, and/or other antibiotic(s) or other non-native bioactive substances can be incorporated in a bioabsorbable polymer coated on and/or incorporated within ECM material included in the pocket construct. The bioabsorbable polymer can be, for example, a bioabsorbable polymer identified herein, or any combination thereof, and can serve to provide sustained release of the non-native bioactive substance(s) in some forms.

Implantable pouch products herein and in particular embodiments wall 12 and/or wall 14, or wall 122 and/or wall 124, can incorporate or in some forms be constituted of xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

When used in the invention, ECM materials or decellularized membranous tissue segments may be essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

In this regard, any porous component of an inventive product (including any ECM material) can have a level or degree of porosity. In certain embodiments, the porosity of a layer or layers of ECM material is lowered by drying the material(s) under compression, for example in the region of segmental lamination providing flange 16 or flange 126 in the pouch products depicted in the Figures herein. In general, compressing a pliable open matrix material, such as a pliable ECM material, increases the material's density and decreases the material's porosity by collapsing pores of the open matrix. As is the case in certain aspects of the invention, when such a material is dried while being compressed, the open matrix structure can become somewhat fixed in this relatively higher density, lower porosity state (i.e., in a relatively more collapsed pore state). The flange region 16 or 126 of the pouch products described herein can be characterized by such a relatively higher or greater density and lower porosity as compared to another region or regions of the pouch product, for example the regions defining walls 12 and 14, or 122 and 124, occurring on either side of an open interior region of the pouch configured to receive all or at least a portion of the electronic or other medical device to be implanted within and in conjunction with the pouch product. The density of flange region 16 or 126 and other regions of the material forming the pouch product can be conventionally determined. For example, the volume and the weight occupied by an amount of the material can be determined, and the volume divided by the weight to provide a density expressed as a unit volume/unit weight (e.g. in grams/cubic centimeter) of the material. In addition, the porosity of flange region 16 or 126 and other regions of the material forming the pouch product can be conventionally determined. For example, mercury intrusion porosimetry can be used to determine the porosity of the materials, e.g. as described by Janis et al., *J. Biomater. Appl.*, May 2012, Vol. 26 No. 8, 1013-1033, which is incorporated herein by reference. It should be noted that different compressing and drying techniques and/or methods, including different degrees of compressing and drying, can be designed through routine experimentation so as to allow for a material layer having an optimal degree of material density and/or porosity for a particular application or procedure.

Segmentally laminated structures used in the invention can include a plurality of ECM material layers bonded together, a plurality of non-ECM material layers bonded together, or a combination of one or more ECM material layers and one or more non-ECM material layers bonded together. Illustratively, two or more ECM segments can be fused or bonded together using a bonding technique, such as chemical cross-linking or vacuum pressing during dehydrating conditions. An adhesive, glue or other bonding agent may also be used in achieving a bond between material layers to form the laminated segment(s) of the pouch products disclosed herein. Suitable bonding agents may include, for example, collagen gels or pastes, gelatin, or other agents including reactive monomers or polymers, for example cyanoacrylate adhesives. A combination of one or more of these with dehydration-induced bonding and/or compression may also be used to bond ECM material sheets or layers, or other sheets of material, to one another.

A variety of dehydration-induced bonding methods can be used to fuse ECM or other sheet material portions together. In one preferred embodiment, multiple layers or other pieces of ECM material and/or other sheet material as described herein are compressed under dehydrating conditions. The term "dehydrating conditions" can include any mechanical or environmental condition which promotes or induces the removal of water from the material. To promote dehydration of the compressed material, at least one of the two surfaces received directly against and compressing the sheet material can be water permeable in some embodiments. Dehydration of the material can optionally be further enhanced by applying blotting material, heating the matrix structure or blowing air, or other inert gas, across the exterior of the compressing surfaces. One particularly useful method of dehydration bonding materials, and preferably collagen-containing materials, is lyophilization. In some forms the lyophilization includes first freezing the materials and then subjecting the frozen materials to lyophilization conditions in which frozen liquid within the materials is removed by sublimation.

Another method of dehydration bonding comprises pulling a vacuum on the sheet material construct or assembly that forms the pouch product or a precursor thereto while simultaneously pressing the construct together. This method is known as vacuum pressing. During vacuum pressing, dehydration of the materials in forced contact with one another effectively bonds the materials to one another, even in the absence of other agents for achieving a bond, although such agents can be used while also taking advantage at least in part of the dehydration-induced bonding. With sufficient compression and dehydration, the materials can be caused to form a generally unitary laminate structure.

In some inventive constructs, a variety of synthetic polymeric materials including but not limited to bioresorbable and/or non-bioresorbable polymeric materials can be used to provide wall materials 12 and/or 14 (or 122 and/or 124) and/or one or more other components of the construct. These or other materials for walls 12 and/or 14 (or 122 and/or 124) can in some embodiments be provided in the form of porous compressible sheet materials, and can be processed to form implantable pouch products having structural features as described herein, including for example flange regions having compressed pore structures and/or denser, less porous and/or thinner characteristics than other regions of the pouch products as described herein. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly (iminocarbonate), copoly(ether-esters) (e.g., PEO/PLA), polyalkylene oxalates, and polyphosphazenes. These or other bioresorbable materials may be used, for example, where only a temporary function is desired, and/or in combination with non-bioresorbable materials where only a temporary participation by the bioresorable material is desired. Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

As well, implantable pouch products herein and in particular wall 12 and/or wall 14, or wall 122 and/or wall 124, thereof can incorporate biocompatible materials derived from a number of biological polymers, which can be naturally occurring or the product of in vitro fermentation, recombinant genetic engineering, and the like. Purified biological polymers can be appropriately formed into a sheet substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

When constructed for use with electronic and other implantable medical devices, inventive pocket structures can be shaped and configured in a variety of manners to accommodate such devices. Pacemakers and defibrillators commonly form part of an inventive system, although various other implantable devices and components can be incorporated into or otherwise used in conjunction with the pocket-providing pouch products described herein. Suitable devices include those used to sense and/or affect bodily function upon implantation and/or for carrying out various other functions in the body. These can be but are not limited to pacing devices, defibrillators, implantable access systems, monitors, stimulators including neurostimulators, ventricular assist devices, pain pumps, infusion pumps and other implantable objects or systems or components thereof, for example, those used to deliver energy and/or substances to the body and/or to help monitor bodily function. Accordingly, implantable products and systems described herein can be implanted at a variety of locations in the body including many different subcutaneous and sub-muscular locations. The outer surfaces of the pacemaker, defibrillator or other implantable medical device can be made of metal or synthetic polymer, and can in certain embodiments be generally smooth and non-receptive to new tissue ingrowth. In this manner the regions of the inventive pocket constructs positioned adjacent to such outer surfaces can generate a new patient tissue pocket structure as discussed herein without causing adhesion of the new tissue to the implantable medical device. Also, as discussed elsewhere herein, inventive constructs, if desired, can be especially configured so that the remodelable characteristics of the device are optimized for the conditions expected at the particular implant location, for example, by performing one or more physical, chemical, biological and/or other manipulations to the remodelable material to account for variables such as the type(s) of tissue occurring at the implant site, the level of blood supply at the site and/or other site specific conditions regarding the implant site of choice.

Inventive structures providing a pocket or space for receiving such devices can be shaped and configured to hold, surround, receive, encapsulate, enclose, cover and/or encase such devices, fully or partially. Pockets and other inventive constructs can be designed to fit a wide range of implantable devices, systems and components thereof. In some instances, a construct will be sized to accommodate a specific device or group of devices from one or more manufacturers. In other instances, a more generic structure will be provided, and the end user will be able to easily modify the structure to accommodate a particular device prior to implantation.

As well, inventive constructs can be shaped and configured to accommodate any leads or other attachments or accessories which may be part of a device or system to be implanted. In this regard, an inventive construct might be provided with one or more openings in the body of the construct that would allow a lead or other similar component to extend from a location within a construct to a location exterior of the construct. Typically, leads are used for patient sensing and, in some cases, for both sensing and stimulation. For example, electrodes on implantable medical leads may detect electrical signals within a patient, such as an electrocardiogram, in addition to delivering electrical stimulation.

Typically, cardiac rhythm management devices (CRMs) are designed to deliver therapeutic stimulation to the heart, for example, in the form of pacing, cardioversion or defibrillation pulses. Such devices generally include a generator and one or more leads. The generator is typically placed below the skin in the chest area (e.g., over or near the breastbone). The generator typically houses a battery and a computer. Energy is stored in the battery until it is needed. The computer receives information on cardiac function via the leads and reacts to that information on the basis of its programming. The lead(s) extend from the generator to one or more cardiac locations.

An implantable cardioverter defibrillator typically includes one or more leads and a pulse generator. The lead(s) monitor the heart rhythm and deliver energy used for pacing and/or defibrillation. Different types of ICDs include but are not limited to single chamber ICDs, dual chamber ICDs, and biventricular ICDs.

A pacemaker can be used to maintain a suitable heart rate and rhythm. Sometimes pacemakers are used to treat fainting spells (syncope), congestive heart failure, hypertrophic cardiomyopathy and other conditions. Different types of pacemakers include but are not limited to single chamber pacemakers; dual chamber pacemakers; and biventricular pacemakers.

A large variety of devices capable of providing stimulation to one or more parts of the body can be used in accordance with the present invention, and in the regard, the targeted implant location for these devices will vary depending on the application. Neurostimulation, muscular stimulation, gastric stimulation and/or other stimulation can be administered via electrodes on the leads and located within or proximate to the target tissue, organ or other body part or system. As examples, implantable medical leads may be positioned proximate to the vagal nerve for delivery of neurostimulation to the vagal nerve. Implantable neurostimulators can be used to send a stimulus, e.g., an electrical signal, via leads to the spine or brain to treat pain and other neurological disorders. Gastrointestinal conditions, severe chronic nausea and vomiting as well as urological disorders can also be treated with appropriate devices as will be understood by those skilled in the art. Chronic pain including back, neck and spinal pain can be treated as well using known devices. Epilepsy and essential tremor including tremors associated with Parkinson's disease and other neurological disorders can be treated in accordance with the present invention. If drug or other delivery systems are used, they will typically include a pump and a catheter for dispensing the substances.

In one illustrative inventive method that involves the implantation of a pacemaker, for example, at a subcutaneous location near the breastbone, the skin above this area is disinfected and otherwise prepared. Thereafter, an incision is made in the skin, and a space for receiving an inventive pouch structure is made beneath the skin, for example, at a sub-muscular location. While the steps of this method can be performed in any suitable order, in some embodiments, the pocket will then be inserted into this space, and optionally secured to its surroundings. Next, the pacemaker is inserted into the pocket with any fillers, accessories, and/or other components also being placed in the pocket, around the pocket, and/or extending from the pocket. Optionally, the device and any accessories will be secured within the pocket and/or to other surroundings. If the pocket is of a type that can be closed, it may then be wholly or partially closed using sutures, staples or other single- or multiple-part closing mechanism, an adhesive and/or in any other suitable manner, being sure to desirably position and otherwise manage any leads or other accessories which might be present. When all parts of the system are desirably positioned in the body, the incision is closed.

Additionally, in certain embodiments, implants of the invention can incorporate an effective amount of one or more antimicrobial agents or agents otherwise useful to inhibit the population of the construct or surrounding tissue with bacteria or other deleterious microorganisms. Illustrative such agents can include, for example, silver compounds, such as silver salts (e.g. silver sulfate), dextran, chitosan, chlorhexidine, rifampin, minocycline, and/or nitric oxide donor compounds. In illustrative embodiments, such an agent or agents can be incorporated throughout the constructs and/or on surfaces and/or selected regions thereof. These or other similar therapeutic agents, e.g. any drug, such as an antibiotic, can be incorporated directly on or in the constructs of the invention, or they can be incorporated with a suitable binder or carrier material, including for instance hydrogel materials. In this regard, the construct can serve to release the one or more agents over time so as to treat the area during healing.

In additional embodiments, the present invention provides medical products that include means or devices as described herein for locating an inventive implant in a patient, and written materials including instructions for use of the means or devices to locate the implant. The products can include the means or devices packaged together with the instructions, e.g. in sterile medical packaging. Related embodiments of the invention include methods for distributing such means or devices, or otherwise conducting business, which include distributing such means or devices for locating inventive implants in a patient, and also distributing information relating the use of such means or devices for locating inventive implant in a patient. Such information can be distributed packaged with the means or device, or separately, e.g. including information or instructions available on a communication network, including a global computer communication network such as the internet.

The present invention also provides, in certain aspects, a line of medical products, wherein a medical product of the invention includes one or more devices, apparatuses or systems of the invention in a sealed package. In some forms of the invention, medical products are provided that include one or more pocket or pocket-like structures such as any of those described herein, and potentially also an electronic or other implantable medical device, enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

Additionally, the package can include indicia to communicate the contents of the package to a person, machine, computer, and/or electronic device. Such indicia may include the dimensions of, the type of materials used to form, and/or other useful information regarding the contents of the package. In certain embodiments, the contents are packaged for sale with instructions for use. For example, in certain preferred embodiments, a medical product includes at least one inventive implant within a sterile package, wherein the packaging can have visible indicia identifying the contents as suitable for implantation in association with an electronic or other implantable medical device, and/or can contain or otherwise be associated with printed materials identifying the contents as such and including information concerning its use.

Listing of Certain Disclosed Embodiments

The following provides an enumerated listing of certain embodiments disclosed herein. It will be understood that unless otherwise specifically indicated, individual features, or combinations of features, described in the Detailed Description hereinabove, can be combined with the following enumerated embodiments to form additional embodiments disclosed herein.

1. An implantable pouch product, comprising:
a first collagen-containing wall material defining a first side of the pouch product;
a second collagen-containing wall material defining a second side of the pouch product;
a first segment of the first collagen-containing wall material laminated to a first segment of the second collagen-containing wall material to define a pocket periphery laminate material;
a pocket defined between a second segment of the first collagen-containing wall material and a second segment of the second collagen-containing wall material that are not laminated to one another, the pocket being bounded by the pocket periphery laminate material;
wherein the first segment of the first collagen-containing wall material comprises lyophilized collagen-containing wall material having a first average density;
wherein the first segment of the second wall material comprises lyophilized collagen-containing wall material having a second average density; and
wherein the pocket periphery laminate material has a third average density, with said third average density being greater than the first average density and the second average density.

2. The product of embodiment 1 wherein the third average density is at least about 50% greater than the first and second average densities.
3. The product of embodiment 1 or 2, wherein the pocket periphery laminate material has an average porosity that is greater than an average porosity of the first collagen-containing wall material and an average porosity of the second collagen-containing wall material.
4. The product of any one of embodiments 1 to 3, wherein the first and second collagen-containing wall materials comprise an extracellular matrix tissue.
5. The product of any one of embodiments 1 to 4, also comprising a plurality of through-openings defined in at least one of said first and second collagen containing wall materials.
6. The product of any one of embodiments 1 to 5, wherein the pocket periphery laminate material extends outward from a periphery of the pocket.
7. The product of any one of embodiments 1 to 5, wherein the pocket periphery laminate material extends inward from a periphery of the pocket.
8. The product of any one of embodiments 1 to 7, also comprising at least one tunnel drain opening extending through the pocket periphery laminate material.
9. The product of embodiment 8, having an opening to the pocket occurring at a side of the product that is generally opposite to the at least one tunnel drain.
10. The product of any one of embodiments 1 to 9, also comprising at least one suture stitch that reinforces the pocket periphery laminate material against delamination, preferably wherein the at least one reinforcement material is attached within the pocket periphery laminate material, adjacent to a terminus of the pocket periphery laminate material, or overlapping a terminus of the pocket periphery laminate material and a region adjacent to the pocket periphery laminate material.
11. The product of any one of embodiments 1 to 9, also comprising at least one reinforcement material, preferably wherein the at least one reinforcement material is attached within the pocket periphery laminate material, adjacent to a terminus of the pocket periphery laminate material, or overlapping a terminus of the pocket periphery laminate material and a region adjacent to the pocket periphery laminate material.
12. The product of any one of embodiments 1 to 11, wherein the first collagen-containing wall material is a laminate material and the second collagen-containing wall material is a laminate material.
13. The product of embodiment 6, also comprising an outer flange extending outward from the pocket periphery laminate material, and outer flange comprising a third segment of the first collagen-containing wall material and a third segment of the second collagen-containing wall material.
14. The product of embodiment 13, wherein said third average density is greater than an average density of the third segment of the first collagen-containing wall material and an average density of the third segment of the second collagen-containing wall material.

15. An implantable pouch product, comprising:
a first wall material defining a first side of the pouch product;
a second wall material defining a second side of the pouch product;
a first segment of the first wall material laminated to a first segment of the second wall material to define a pocket periphery laminate material;
a pocket defined between a second segment of the first wall material and a second segment of the second wall material that are not laminated to one another, the pocket being bounded by the pocket periphery laminate material.

16. The product of embodiment 15, wherein:
the pocket periphery laminate material has an inner perimeter; and
the product has at least one drainage opening for draining liquid from the pocket, the at least one drainage opening including at least one opening in the first wall material or the second wall material occurring within 3 mm of the inner perimeter of the pocket periphery laminate material and/or at least one tunnel drain opening extending through the pocket periphery laminate material.

17. The product of embodiment 15 or 16, wherein:
the pocket periphery laminate material comprises collapsed pore structures of the first segment of the first wall material and the first segment of the second wall material.

18. The product of any one of embodiments 15 to 17, wherein:
the first segment of the first wall material has an average density greater than that of the second segment of the first wall material; and
the first segment of the second wall material has an average density greater than that of the second segment of the second wall material.

19. The product of any one of embodiments 15 to 18, wherein:
the first segment of the first wall material has an average porosity greater than that of the second segment of the first wall material; and
the first segment of the second wall material has an average density greater than that of the second segment of the second wall material.

20. The product of any one of embodiments 15 to 19, wherein:
the first segment of the first wall material has an average thickness less than that of the second segment of the first wall material; and
the first segment of the second wall material has an average thickness less than that of the second segment of the second wall material.

21. The product of any one of embodiments 15 to 20, wherein:
the first wall material comprises a collagen-containing material.

22. The product of any one of embodiments 15 to 21, wherein:
the second wall material comprises a collagen-containing material.

23. The product of embodiment 21 or 22, wherein:
the collagen-containing material is a decellularized membranous tissue segment.

24. The product of embodiment 23, wherein the decellularized membranous tissue segment is an extracellular matrix tissue material.

25. The product of embodiment 24, wherein the extracellular matrix tissue material comprises submucosa.

26. The product of any one of embodiments 15 to 25, also comprising a plurality of through-openings defined in at least one of said first and second wall materials.

27. The product of embodiment 26, comprising a plurality of through-openings in both said first and second wall materials.

28. The product of any one of embodiments 15 to 27, wherein the pocket periphery laminate material extends outward from a periphery of the pocket.

29. The product of any one of embodiments 15 to 27, wherein the pocket periphery laminate material extends inward from a periphery of the pocket.

30. The product of any one of embodiments 15 to 29, also comprising at least one suture stitch within the pocket periphery laminate material or proximate to an end of the pocket periphery laminate material, the at least one suture stitch reinforcing the pocket periphery laminate material against delamination.

31. The product of any one of embodiments 15 to 29, also comprising at least one reinforcement material within the pocket periphery laminate material or proximate to an end of the pocket periphery laminate material, and at least one reinforcement material reinforcing the pocket periphery laminate material against delamination.

32. The product of any one of embodiments 15 to 31, wherein the first wall material is a laminate material and the second wall material is a laminate material.

33. The product of embodiment 28, also comprising an outer flange extending outward from the pocket periphery laminate material, and outer flange comprising a third segment of the first collagen-containing wall material and a third segment of the second collagen-containing wall material.

34. The product of embodiment 33, wherein the third segment of the first wall material has an average porosity greater than that of the first segment of the first wall material, has an average density greater than that of the first segment of the first wall material, and/or has an average thickness less than that of the first segment of the first wall material.

35. The product of embodiment 33 or 34, wherein the third segment of the second wall material has an average porosity greater than that of the first segment of the second wall material, has an average density greater than that of the first segment of the second wall material, and/or has an average thickness less than that of the first segment of the second wall material.

36. The product of any one of embodiments 1 to 14, wherein the first collagen-containing wall material and the second collagen-containing wall material are provided by a single piece of collagen containing wall material.

37. The product of embodiment 36, wherein the single piece of collagen containing wall material has a fold between the first collagen-containing wall material and the second collagen-containing wall material.

38. The product of embodiment 37, wherein the fold defines at least a portion of an outer periphery of the implantable pouch product.

39. The product of any one of embodiments 36 to 38, wherein the single piece of collagen containing wall material is a decellularized segment of a tissue structure having a native tube or native chamber shape, and preferably wherein the first collagen containing wall material is from a first side of the tissue structure and the second collagen containing wall material is from a second side of the tissue structure opposite the first side of the tissue structure.

40. The product of embodiment 39, wherein the tissue structure is intestinal tissue, urinary bladder tissue, or stomach tissue.

41. The product of any one of embodiments 37 to 40, wherein the fold defines at least a portion of an outer periphery of the implantable pouch product, and wherein said at least a portion of the outer periphery has a curved shape; and preferably wherein said curved shape is a convexly curved shape formed from a naturally convexly curved fold of the tissue structure.

42. The product of any one of embodiments 37 to 41, wherein the pocket periphery laminate material begins at the fold and extends inward therefrom, or begins inward of the fold and extends inward on the pouch product a distance.

43. The product of any one of embodiments 15 to 35, wherein the first wall material and the second wall material are provided by a single piece of wall material.

44. The product of embodiment 43, wherein the single piece of wall material has a fold between the first wall material and the second wall material.

45. The product of embodiment 44, wherein the fold defines at least a portion of an outer periphery of the implantable pouch product.

46. The product of any one of embodiments 43 to 45, wherein the single piece of wall material is a decellularized segment of a tissue structure having a native tube or native chamber shape, and preferably wherein the first wall material is from a first side of the tissue structure and the second wall material is from a second side of the tissue structure opposite the first side of the tissue structure.

47. The product of embodiment 46, wherein the isolated tissue is intestinal tissue, urinary bladder tissue, or stomach tissue.

48. The product of any one of embodiments 44 to 47, wherein the fold defines at least a portion of an outer periphery of the implantable pouch product, and wherein said at least a portion of the outer periphery has a curved shape; and preferably wherein said curved shape is a convexly curved shape formed from a naturally convexly curved fold of the tissue structure.

49. The product of any one of embodiments 44 to 48, wherein the pocket periphery laminate material begins at the fold and extends inward therefrom, or begins inward of the fold and extends inward on the pouch product a distance.

50. An implantable product, comprising:
an implantable pouch product of any one of embodiments 1 to 49; and
a medical device received in the pocket of the implantable pouch product.

51. The implantable product of embodiment 50, wherein:
the medical device has an outer surface that is not receptive to patient tissue ingrowth.

52. The implantable product of embodiment 50 or 51, wherein the medical device is an electronic medical device.

53. The implantable product of any one of embodiments 50 to 52, wherein the medical device is a cardiac pacemaker or defibrillator.

54. The implantable product of embodiment 53, also comprising electric leads extending from the pacemaker or defibrillator.

55. The implantable product of embodiment 54, wherein the electric leads extend through a tunnel opening through the pocket periphery laminate material of the pouch product.

56. A method for making an implantable pouch product, comprising:
providing a first wall material;
providing a second wall material;
laminating a first segment of the first wall material to a first segment of the second wall material to define a pouch periphery laminate material;
said laminating conducted so as to leave a pocket defined by a second segment of the first wall material and a second segment of the second wall material that are not laminated to one another, the pocket being bounded by the pouch periphery laminate material.

57. The method of embodiment 56, wherein said laminating comprises:
providing a compressed construct having the first segment of the first wall material, in wetted condition, compressed against the first segment of the second wall material in wetted condition; and
freezing the compressed construct; and
drying the compressed construct by lyophilization.

58. The method of embodiment 56 or 57, also comprising:
cutting a plurality of openings in the second segment of the first wall material.

59. The method of embodiment 58, also comprising:
cutting a plurality of openings in the second segment of the second wall material.

60. The method of any one of embodiments 56 to 59, wherein the first wall material and the second wall material are provided by a single piece of wall material.

61. The method of embodiment 60, wherein a fold occurs between the first wall material and the second wall material, and wherein the pouch periphery laminate material begins at the fold or begins inward of the fold.

62. The method of embodiment 61, wherein the fold defines at least a portion of an outer periphery of the implantable pouch product.

63. The method of embodiment 62, wherein said at least a portion of the outer periphery of the implantable pouch product has a curved shape, preferably a convex curved shape.

The use of the terms "a" and "an" and "the" and similar referents in the context of describing the embodiments especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any nonclaimed element as essential to the practice of the invention.

All publications cited in this specification are herein incorporated by reference as if each individual publication were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. An implantable pouch product, comprising:
   a first collagen-containing wall material defining a first side of the pouch product;
   a second collagen-containing wall material defining a second side of the pouch product; said first collagen-containing wall material and said second collagen-containing wall material connected by a fold between said first collagen-containing wall material and said second collagen-containing wall material;
   a first segment of the first collagen-containing wall material laminated to a first segment of the second collagen-containing wall material to define a pocket periphery laminate material;
   a pocket defined between a second segment of the first collagen-containing wall material and a second segment of the second collagen-containing wall material that are not laminated to one another, the pocket being bounded by the pocket periphery laminate material;
   wherein at least a portion of the pocket periphery laminate material forms a bonded flange positioned inward of the fold occurring between the first collagen-containing wall material and the second collagen-containing wall material;
   the first segment of the first collagen-containing wall material has an average density greater than that of the second segment of the first collagen-containing wall material; and
   the first segment of the second collagen-containing wall material has an average density greater than that of the second segment of the second collagen-containing wall material.

2. The product of claim 1, wherein the pocket periphery laminate material has an average porosity that is greater than an average porosity of the first collagen-containing wall material and an average porosity of the second collagen-containing wall material.

3. The product of claim 1, wherein the first and second collagen-containing wall materials comprise an extracellular matrix tissue.

4. The product of claim 1, also comprising a plurality of through-openings defined in at least one of said first and second collagen containing wall materials.

5. The product of claim 1, wherein the pocket periphery laminate material extends outward from a periphery of the pocket.

6. The product of claim 1, wherein the pocket periphery laminate material extends inward from a periphery of the pocket.

7. The product of claim 1, also comprising at least one tunnel drain opening extending through the pocket periphery laminate material.

8. The product of claim 7, having an opening to the pocket occurring at a side of the product that is generally opposite to the at least one tunnel drain.

9. The product of claim 1, also comprising at least one suture stitch that reinforces the pocket periphery laminate material against delamination.

10. The product of claim 1, also comprising at least one reinforcement material, wherein the at least one reinforcement material is attached within the pocket periphery laminate material, adjacent to a terminus of the pocket periphery laminate material, or overlapping a terminus of the pocket periphery laminate material and a region adjacent to the pocket periphery laminate material.

11. The product of claim 1, wherein the first collagen-containing wall material is a laminate material and the second collagen-containing wall material is a laminate material.

12. The product of claim 5, also comprising an outer flange extending outward from the pocket periphery laminate material, and outer flange comprising a third segment of the first collagen-containing wall material and a third segment of the second collagen-containing wall material.

13. An implantable product, comprising:
    an implantable pouch product of claim 1; and
    a medical device received in the pocket of the implantable pouch product.

* * * * *